United States Patent
Karpas et al.

(10) Patent No.: US 9,750,914 B2
(45) Date of Patent: Sep. 5, 2017

(54) METHODS FOR FABRICATING OBJECTS USING INVESTMENT MOLDING TECHNIQUES

(71) Applicant: MetaMason, Inc., Los Angeles, CA (US)

(72) Inventors: Leslie Oliver Karpas, Los Angeles, CA (US); Aaron M. Ryan, Los Angeles, CA (US)

(73) Assignee: MetaMason, Inc., Los Angeles, CA (US)

( * ) Notice: Subject to any disclaimer, the term of this patent is extended or adjusted under 35 U.S.C. 154(b) by 458 days.

(21) Appl. No.: 14/173,549

(22) Filed: Feb. 5, 2014

(65) Prior Publication Data

US 2015/0035200 A1    Feb. 5, 2015

Related U.S. Application Data

(60) Provisional application No. 61/861,376, filed on Aug. 1, 2013.

(51) Int. Cl.
*A61M 16/06* (2006.01)
*B29C 67/00* (2017.01)
(Continued)

(52) U.S. Cl.
CPC .... *A61M 16/0605* (2014.02); *A61M 16/0666* (2013.01); *A61M 16/0683* (2013.01);
(Continued)

(58) Field of Classification Search
None
See application file for complete search history.

(56) References Cited

U.S. PATENT DOCUMENTS

| | | |
|---|---|---|
| 5,059,266 A | 10/1991 | Yamane et al. |
| 5,134,569 A | 7/1992 | Masters |

(Continued)

FOREIGN PATENT DOCUMENTS

| | | |
|---|---|---|
| CN | 101516427 A | 8/2009 |
| EP | 2514775 A1 | 10/2012 |

(Continued)

OTHER PUBLICATIONS

International Search Report and Written Opinion for International Application No. PCT/SG2013/000524, Search Completed Apr. 2, 2014, 12 pgs.

(Continued)

*Primary Examiner* — Edmund Lee
(74) *Attorney, Agent, or Firm* — KPPB LLP

(57) ABSTRACT

Systems and methods in accordance with embodiments of the invention fabricate objects using investment molding techniques. In one embodiment, a method of fabricating an object includes: fabricating a subassembly including a plurality of volumes; where each volume is defined by the homogenous presence or absence of a material; where fabricating the subassembly includes using an additive manufacturing process; where at least one of the plurality of volumes defines a shape that is to exist in the object to be fabricated; where at least a first of the plurality of volumes includes a first dissolvable material; dissolving the first dissolvable material; where the dissolution of the first dissolvable material does not dissolve at least one other material within the subassembly; forming at least one cavity within the subassembly; and introducing an additive material into the at least one cavity.

21 Claims, 23 Drawing Sheets

(51) Int. Cl.
| | |
|---|---|
| *B29C 33/52* | (2006.01) |
| *G06F 17/50* | (2006.01) |
| *B33Y 10/00* | (2015.01) |
| *B33Y 50/02* | (2015.01) |
| *B33Y 80/00* | (2015.01) |
| *A61M 16/08* | (2006.01) |
| *G06K 9/00* | (2006.01) |
| *G06T 17/00* | (2006.01) |
| *B29K 101/12* | (2006.01) |

(52) U.S. Cl.
CPC .... *A61M 16/0816* (2013.01); *A61M 16/0875* (2013.01); *B29C 33/52* (2013.01); *B29C 67/0055* (2013.01); *B29C 67/0088* (2013.01); *B29C 67/0092* (2013.01); *B33Y 10/00* (2014.12); *B33Y 50/02* (2014.12); *B33Y 80/00* (2014.12); *G06F 17/50* (2013.01); *G06K 9/0061* (2013.01); *G06K 9/00281* (2013.01); *G06T 17/00* (2013.01); *A61M 2016/0661* (2013.01); *A61M 2207/00* (2013.01); *B29K 2101/12* (2013.01); *B29K 2995/0059* (2013.01); *B29K 2995/0062* (2013.01)

(56) References Cited

U.S. PATENT DOCUMENTS

| | | | |
|---|---|---|---|
| 6,129,872 | A | 10/2000 | Jang |
| 6,139,793 | A | 10/2000 | Vanderwal |
| 6,143,378 | A | 11/2000 | Harwell et al. |
| 6,174,481 | B1 * | 1/2001 | Holowczak ......... B29C 33/3857 264/220 |
| 6,245,265 | B1 * | 6/2001 | Chung .................... B29C 33/52 164/132 |
| 6,375,880 | B1 * | 4/2002 | Cooper ................... B29C 33/52 264/138 |
| 6,616,885 | B2 * | 9/2003 | Lombardi ........... B29C 67/0062 264/138 |
| 6,790,403 | B1 | 9/2004 | Priedeman, Jr. et al. |
| 7,087,200 | B2 | 8/2006 | Taboas et al. |
| 7,168,935 | B1 | 1/2007 | Taminger et al. |
| 7,816,127 | B2 | 10/2010 | Nomura |
| 8,062,023 | B2 * | 11/2011 | Appleby ............... B23P 15/246 156/245 |
| 8,246,888 | B2 | 8/2012 | Hopkins et al. |
| 8,459,280 | B2 | 6/2013 | Swanson et al. |
| 8,460,755 | B2 | 6/2013 | Rodgers |
| 9,102,099 | B1 | 8/2015 | Karpas et al. |
| 2004/0079374 | A1 | 4/2004 | Thornton |
| 2006/0175034 | A1 | 8/2006 | Okhuysen-Caredenas et al. |
| 2008/0006273 | A1 | 1/2008 | Thornton |
| 2008/0060652 | A1 | 3/2008 | Selvarajan et al. |
| 2008/0110869 | A1 | 5/2008 | Chen |
| 2008/0118655 | A1 | 5/2008 | Kritchman |
| 2010/0181706 | A1 | 7/2010 | Ruuttu et al. |
| 2010/0191360 | A1 | 7/2010 | Napadensky et al. |
| 2010/0270274 | A1 | 10/2010 | Taminger et al. |
| 2011/0045120 | A1 * | 2/2011 | Higashi .................. B22F 5/007 425/552 |
| 2011/0068502 | A1 * | 3/2011 | Basseas ............. B29C 33/0016 264/219 |
| 2011/0076495 | A1 | 3/2011 | Batchelder et al. |
| 2011/0109016 | A1 | 5/2011 | Fuwa et al. |
| 2011/0203937 | A1 | 8/2011 | Sidhu et al. |
| 2012/0252107 | A1 | 10/2012 | Self |
| 2013/0011624 | A1 | 1/2013 | Takenaka |
| 2013/0215197 | A1 | 8/2013 | Hays et al. |
| 2013/0241114 | A1 | 9/2013 | Ravich et al. |
| 2014/0061974 | A1 | 3/2014 | Tyler |
| 2015/0217517 | A1 | 8/2015 | Karpas et al. |
| 2015/0321420 | A1 | 11/2015 | Ryan et al. |

FOREIGN PATENT DOCUMENTS

| | | |
|---|---|---|
| JP | 2002331275 A | 11/2002 |
| WO | 0009307 | 2/2000 |
| WO | 03089215 | 10/2003 |
| WO | 2006020279 A2 | 2/2006 |
| WO | 2011119112 A1 | 9/2011 |
| WO | 2013126981 A1 | 9/2013 |
| WO | 2015017829 A2 | 2/2015 |
| WO | 2015017829 A8 | 3/2015 |
| WO | 2015120200 A1 | 8/2015 |

OTHER PUBLICATIONS

International Search Report and Written Opinion for International Application PCT/US2014/049481, completed Oct. 10, 2014, 8 pgs.
"3D printing parts with overhanfs using new soluble support material", 3D printer and 3D printing news, Feb. 28, 2013, 3 pgs.
"RTV Molding With PolyJet or FDM Patterns", Stratasys for a 3D World, 3 pgs.
Frick, "How to 3D Print Plastic Molds and Tooling", Machine Design, 7 pgs.
International Preliminary Report on Patentability for International Application PCT/US2015/014689, Issued Aug. 9, 2016, Mailed Aug. 18, 2016, 8 Pgs.
International Search Report and Written Opinion PCT/US2015/014689, Search Completed Mar. 31, 2015, dated Apr. 21, 2015, 10 Pgs.
International Preliminary Report on Patentability for International Application PCT/US2014/049481, Report dated Feb. 2, 2016, dated Feb. 11, 2016, 6 Pgs.

* cited by examiner

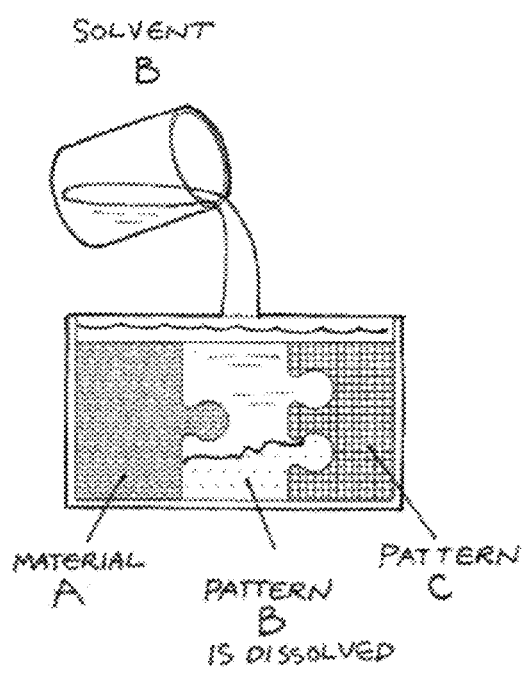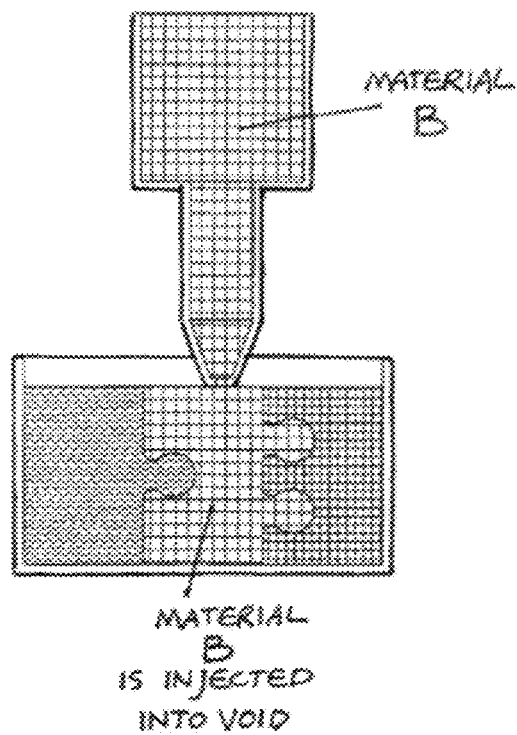
FIG. 4I
FIG. 4J

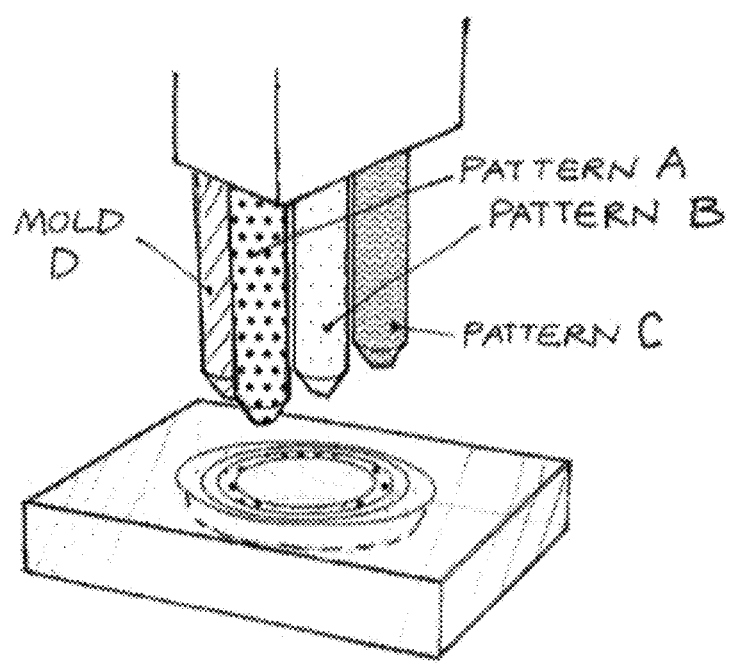
FIG. 5C
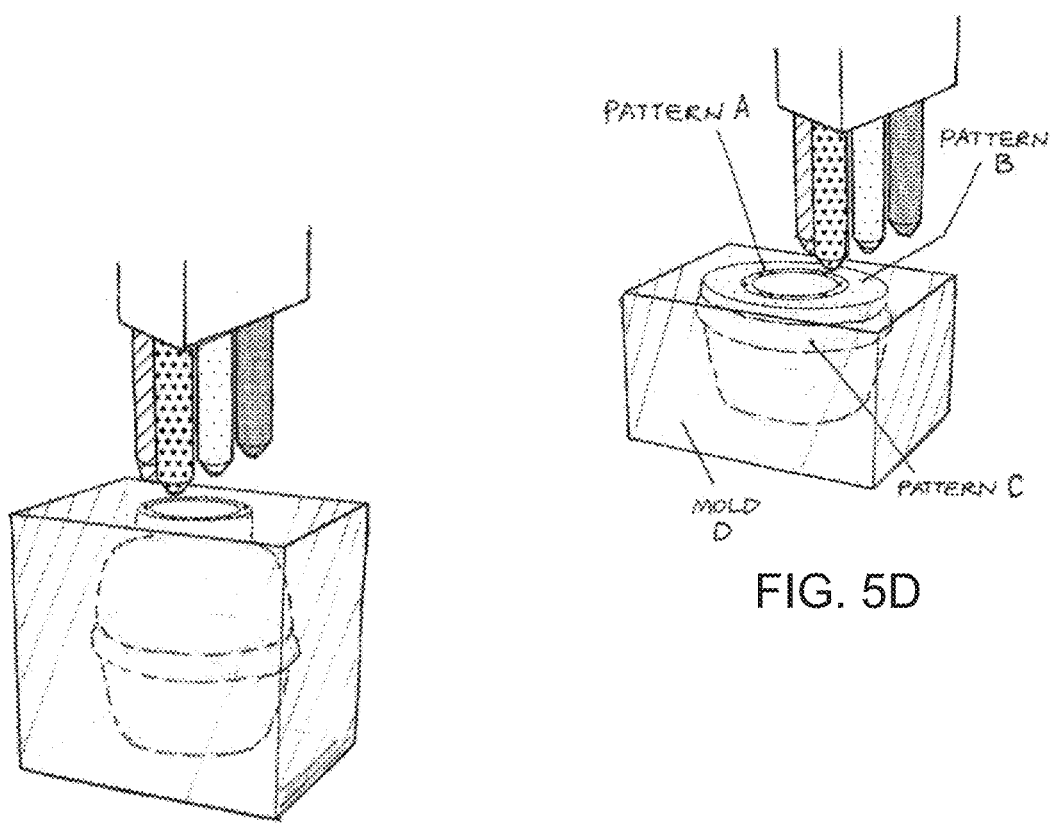
FIG. 5D
FIG. 5E

METHODS FOR FABRICATING OBJECTS USING INVESTMENT MOLDING TECHNIQUES

CROSS-REFERENCE TO RELATED APPLICATIONS

The current application claims priority to U.S. Provisional Patent Application No. 61/861,376, filed Aug. 1, 2013, the disclosure of which is hereby incorporated by reference.

FIELD OF THE INVENTION

The present invention generally relates to additive manufacturing techniques.

BACKGROUND

'Additive manufacturing,' or '3D Printing,' is a term that typically describes a manufacturing process whereby a 3D model of an object to be fabricated is provided to an apparatus (e.g. a 3D printer), which then autonomously fabricates the object by depositing successive layers of material that represent cross-sections of the object; generally, the deposited layers of material fuse (or otherwise solidify) to form the final object. Because of their relative versatility, additive manufacturing techniques have generated much interest. Nonetheless, additive manufacturing techniques are burdened with several limitations. For example, additive manufacturing processes are generally limited to depositing materials that are compatible with the unique process, e.g. materials that can be deposited in a layer-by-layer manner and can subsequently be made to fuse (or otherwise solidify).

SUMMARY OF THE INVENTION

Systems and methods in accordance with embodiments of the invention fabricate objects using additive manufacturing techniques in conjunction with casting and other similar techniques; the techniques used in tandem as described below can be understood to be 'investment molding' techniques. In one embodiment, a method of fabricating an object includes: fabricating a subassembly including a plurality of volumes; where each volume is defined by the homogenous presence or absence of a material; where fabricating the subassembly includes using an additive manufacturing process; where at least one of the plurality of volumes defines a shape that is to exist in the object to be fabricated; where at least a first of the plurality of volumes includes a first dissolvable material; dissolving the first dissolvable material; where the dissolution of the first dissolvable material does not dissolve at least one other material within the subassembly; forming at least one cavity within the subassembly; and introducing an additive material into the at least one cavity.

In another embodiment, the subassembly is additively manufactured to include at least one cavity.

In yet another embodiment, a second volume includes a second dissolvable material; the dissolution of the first dissolvable material does not dissolve the second dissolvable material; a cavity is formed within the subassembly by the dissolution of the first dissolvable material; and the additive material is introduced into the cavity formed by the dissolution of the first dissolvable material, conforms to the shape of the cavity, and thereby forms an integral part of the object to be fabricated.

In still yet another embodiment, the subassembly includes a volume that is defined by the homogenous presence of a material, where the material acts to support the subassembly when the first dissolvable material is dissolved and when the additive material is introduced into the cavity.

In a further embodiment, the method further includes removing the material that acts to support the subassembly when the first dissolvable material is dissolved and when the additive material is introduced into the cavity.

In a yet further embodiment, the removal of the material that acts to support the subassembly when the first dissolvable material is dissolved and when the additive material is introduced into the cavity is achieved mechanically.

In a still further embodiment, the removal of the material that acts to support the subassembly when the first dissolvable material is dissolved and when the additive material is introduced into the cavity is achieved by dissolving the material.

In a still yet further embodiment, the first dissolvable material is one of: prolyvinyl alcohol (PVA), high impact polystyrene (HIPS), polylactic acid (PLA), acrylonitrile butadiene styrene (ABS), nylon, polycarbonate, glucose, glucose gelatin, polyethylene terephthalate (PET), polycarprolactone (PCL), low-density polyethylene (LDPE), high density polyethylene (HDPE), polymethylpentene (PMP), polypropylene (PP), polytetrafluoroethylene (PTFE), polyvinyl chloride (PVC), and mixtures thereof.

In another embodiment, dissolving the first dissolvable material includes subjecting the first dissolvable material to a respective solvent.

In yet another embodiment, the solvent is one of: water, terpene, limonine, sodium hydroxide, acetone, acetic acid, dichloromethane, respective enzymes, acetaldehyde, acetic anhydride, acetone, hydrofluoric acid, trifluoroacetic acid, dilute acetic acid (50%), hydrochloric acid (37%), nitric acid, sulfuric acid, ethyl alcohol, isobutyl alcohol, methyl alcohol, n-butyl alcohol propyl alcohol, ammonium hydroxide, aniline, aqua regia, benzaldehyde, benzene, carbon tetrachloride, caustic soda (NaOH), chlorobenzene, chloroform, cyclohexane, esters, ether, diethyl ether, isopropyl ether, methyl ethyl, hexane, hydrazine, hydrogen peroxide, methylene chloride, petroleum ether, phenol, sodium hydroxide, tetrahydrofuran, toluene, trichloroethylene, trimethylpentane, xylene, and mixtures thereof.

In still another embodiment, a second volume defines a body portion and a sprue portion that extends from the body portion to the external surface of the subassembly; and the introduction of the additive material into the at least one cavity includes introducing the additive material into the body portion through the sprue portion.

In still yet another embodiment, the dissolution of the first dissolvable material occurs subsequent to the introduction of the additive material into the second volume; and the first volume and the second volume are defined such that when the additive material is introduced into the second volume beyond a threshold extent, and the additive material achieves a solid state, the additive material provides sufficient structural support to maintain the spatial relationship between the first volume and the second volume when the first dissolvable material is dissolved.

In a further embodiment, the additive material is introduced into the second volume to the extent that the additive material conforms to the shape of at least a part of the sprue portion, and upon solidification, thereby provides sufficient structural support to maintain the spatial relationship between the first volume and the second volume when the first dissolvable material is dissolved.

In a yet further embodiment, the subassembly includes a volume that is defined by the presence of a material, where the material acts to support the subassembly when the first dissolvable material is dissolved and when the additive material is introduced into the second volume.

In a still further embodiment, the method further includes removing the material that acts to support the subassembly when the first dissolvable material is dissolved and when the additive material is introduced into the second volume.

In a still yet further embodiment, the removal of the material that acts to support the subassembly when the first dissolvable material is dissolved and when the additive material is introduced into the second volume is achieved mechanically.

In another embodiment, the removal of the material that acts to support the subassembly when the first dissolvable material is dissolved and when the additive material is introduced into the second volume is achieved by dissolving the material.

In yet another embodiment, the first dissolvable material is one of: prolyvinyl alcohol (PVA), high impact polystyrene (HIPS), polylactic acid (PLA), acrylonitrile butadiene styrene (ABS), nylon, polycarbonate, glucose, glucose gelatin, polyethylene terephthalate (PET), polycarprolactone (PCL), low-density polyethylene (LDPE), high density polyethylene (HDPE), polymethylpentene (PMP), polypropylene (PP), polytetrafluoroethylene (PTFE), polyvinyl chloride (PVC), and mixtures thereof.

In still yet another embodiment, dissolving the first dissolvable material includes subjecting the first dissolvable material to a respective solvent.

In a further embodiment, the solvent is one of: water, terpene, limonine, sodium hydroxide, acetone, acetic acid, dichloromethane, respective enzymes, acetaldehyde, acetic anhydride, acetone, hydrofluoric acid, trifluoroacetic acid, dilute acetic acid (50%), hydrochloric acid (37%), nitric acid, sulfuric acid, ethyl alcohol, isobutyl alcohol, methyl alcohol, n-butyl alcohol propyl alcohol, ammonium hydroxide, aniline, aqua regia, benzaldehyde, benzene, carbon tetrachloride, caustic soda (NaOH), chlorobenzene, chloroform, cyclohexane, esters, ether, diethyl ether, isopropyl ether, methyl ethyl, hexane, hydrazine, hydrogen peroxide, methylene chloride, petroleum ether, phenol, sodium hydroxide, tetrahydrofuran, toluene, trichloroethylene, trimethylpentane, xylene, and mixtures thereof.

In a yet further embodiment, the volume that defines a shape that is to exist in the object to be fabricated is occupied by solid material in the fabricated object.

BRIEF DESCRIPTION OF THE DRAWINGS

FIGS. 4A-4L illustrate the principles of the process outlined in FIG. 3 in accordance with embodiments of the invention.

FIGS. 5A-5L illustrate the fabrication of a CPAP Coupling, whereby a predetermined arrangement of patterns is additively manufactured using dissolvable materials, and the dissolvable materials are subsequently dissolved and replaced by materials that constitute the component to be fabricated in accordance with embodiments of the invention.

DETAILED DESCRIPTION

Figure 1:
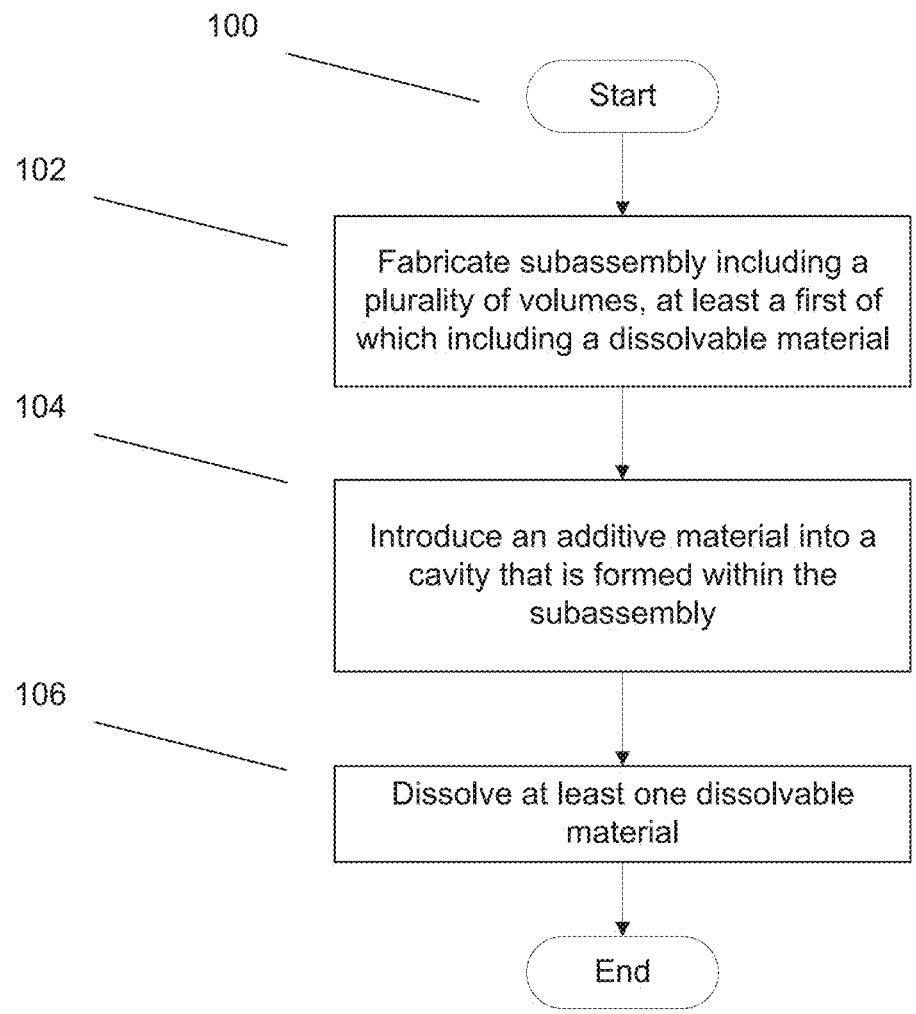
FIG. 1 illustrates a process for fabricating components where a material is inserted into a cavity that is formed within a subassembly, and a dissolvable material within the subassembly is thereafter dissolved in accordance with embodiments of the invention.

Turning now to the drawings, systems and methods for fabricating components using additive manufacturing techniques in conjunction with casting or other similar techniques are illustrated. The techniques used in tandem as described below can be understood to be investment molding techniques. In many embodiments, a subassembly including a plurality of volumes is additively manufactured, where at least one of the volumes includes a dissolvable material that is subsequently dissolved, and a different additive material is introduced into a volume that is a cavity that is made to exist within the subassembly. In several embodiments, the subassembly includes a sprue portion that acts to facilitate the insertion of a material into a cavity within it, and thereafter acts as a support so as to maintain the spatial relationship between two volumes within the subassembly. In a number of embodiments, the dissolution of a dissolvable material within the pattern defines the cavity in which a material an additive material is introduced; generally, the subassembly can include multiple dissolvable materials that are iteratively dissolved and replaced by introduced additive materials.

Since its inception, additive manufacturing, or '3D Printing', has generated much interest from manufacturing communities because of the seemingly unlimited potential that these fabrication techniques can offer. For example, these techniques have been demonstrated to produce any of a variety of distinct and intricate geometries, with the only input being the final shape of the object to be formed. In many instances, a 3D rendering of an object is provided electronically to a '3D Printer', which then fabricates the object. Many times, a 3D Printer is provided with a CAD File, a 3D Model, or instructions (e.g. via G-code), and the 3D Printer thereby fabricates the object. Importantly, as can be inferred, these processing techniques can be used to avoid heritage manufacturing techniques that can be far more resource intensive and inefficient. The relative simplicity and versatility of this process can pragmatically be used in any of a variety of scenarios including for example to allow for rapid prototyping and/or to fabricate components that are highly customized for particular consumers. For example, shoes that are specifically adapted to fit a particular individual can be additively manufactured. Indeed, U.S. Provisional Patent Application No. 61/861,376 discloses the manufacture of customized medical devices and apparel using additive manufacturing techniques; U.S. Provisional Patent Application No. 61/861,376 is hereby incorporated by reference. It should also be mentioned that the cost of 3D printers has recently noticeably decreased, thereby making additive manufacturing processes an even more viable fabrication methodology.

In spite of these advantages, additive manufacturing techniques are not without their limitations. For example, additive manufacturing techniques are generally limited to manufacturing objects that are composed of materials that are compatible with the deposition and fusion (or other solidification—e.g. binding and/or curing) that occur during the additive manufacturing process. In many instances, it may be desirable to additively manufacture an object from materials that might not easily lend themselves to additively manufacturing processes. Thus, in many embodiments, additive manufacturing processes are used in conjunction with casting or other similar techniques to fabricate objects. In many embodiments, a subassembly including a plurality of volumes—a volume being defined by the homogenous presence or absence of a distinct material—where one of the volumes includes a dissolvable material, is additively manufactured, the dissolvable material is thereafter made to dissolve, and a material is inserted into a cavity that is made to exist within the subassembly (e.g. via a casting technique). The post-processing of the additively manufactured sub-assembly can be thought of as the 'build-up' aspect of the described fabrication techniques. These processes also regard the manufacture of a subassembly including multiple dissolvable volumes, and the dissolution and introduction of additive materials can be iterated any number of times in order to create more complex geometries in accordance with embodiments of the invention. In this way, these techniques can take advantage of the versatility that additive manufacturing offers as well as the unique material selection that casting and other similar techniques can offer. These techniques can be termed 'investment molding techniques' and are now discussed in greater detail below.

Investment Molding Techniques

In many embodiments of the invention, an object is fabricated using additive manufacturing processes in conjunction with casting or other similar techniques. For example, in numerous embodiments, a subassembly is additively manufactured that includes a plurality of volumes, at least one of which includes a dissolvable material, the dissolvable material is thereafter dissolved, and a material is inserted into a cavity that is formed within the subassembly. In this context, the subassembly can be understood to be defining a template for the fabrication of an object; thus, in numerous embodiments, the subassembly defines at least one shape that is to exist in the fabricated object. In many embodiments, the subassembly is additively manufactured to include the cavity. In a number of embodiments, the cavity is formed by the dissolution of the dissolvable material, and a material is thereafter inserted into the cavity. As can be appreciated, the dissolution of dissolvable materials and the introduction of materials into cavities made to exist can be iterated any number of times in the fabrication of an object in accordance with embodiments of the invention, and objects of varying degrees of intricacy can thereby be fabricated. In this way, the additively manufactured subassembly can be understood to be establishing a template for an object to be fabricated, and the dissolution of dissolvable materials and introduction of additive materials can thereafter be implemented to build-up the object using the subassembly that acts as a template. Accordingly, an object can be fabricated, using additive manufacturing processes, from materials that do not easily lend themselves to additive manufacturing processes.

As an example, a process for fabricating an object including the formation of at least one cavity within a subassembly and the use of at least one dissolvable material in accordance with embodiments of the invention is illustrated in FIG. 1. The process 100 includes fabricating 102 a subassembly including a plurality of volumes, at least a first of which including a dissolvable material. Generally, the volumes can be understood to be defined by the homogenous presence or absence of a distinct material. In other words, the subassembly can be understood to be an arrangement of patterns, where the patterns correspond to the aforementioned volumes defined by the homogenous presence or absence of distinct materials. Further, a volume that is defined by the homogenous absence of a distinct material can be characterized as a 'void space', a 'negative space,' or 'a cavity.' In many instances, at least one of the plurality of volumes defines a shape that is to exist in the object to be fabricated. For example, in some embodiments, the object to be fabricated includes solid material in the aforementioned 'defined shape.' In a number of embodiments, the fabricated object includes a void space that conforms to the aforementioned 'defined shape.' In several embodiments, one of the plurality of volumes defines a cavity within the subassembly.

Typically, the fabrication 102 of the subassembly is accomplished via additive manufacturing processes. It should of course be understood that any suitable additive manufacturing process can be implemented in accordance with embodiments of the invention. In many instances, at least one of the plurality of volumes includes a dissolvable material. For example, the dissolvable material could be one of: prolyvinyl alcohol (PVA), high impact polystyrene (HIPS), polylactic acid (PLA), acrylonitrile butadiene styrene (ABS), nylon, polycarbonate, glucose, and glucose gelatin. Note that these materials are dissolvable insofar as: PVA is soluble in water; HIPS is soluble in limonine or terpene (citric acid); PLA is soluble in sodium hydroxide (caustic soda); ABS is soluble in acetone; nylon is soluble in acetic acid; polycarbonate is soluble in dichloromethane; and glucose and glucose gelatin are soluble in respective enzymes. Of course, although several dissolvable materials are mentioned, along with respective solvents, it should of course be understood that any dissolvable material can be incorporated in the manufacture in accordance with embodiments of the invention. For example, the dissolvable material can also be one of: polyethylene terephthalate (PET), polycarprolactone (PCL), low-density polyethylene (LDPE), high density polyethylene (HDPE), polymethylpentene (PMP), polypropylene (PP), polytetrafluoroethylene (PTFE), polyvinyl chloride (PVC), and mixtures thereof. Similarly, the solvent used to dissolve the dissolvable material can be one of: acetaldehyde, acetic anhydride, acetone, hydrofluoric acid, trifluoroacetic acid, dilute acetic acid (50%), hydrochloric acid (37%), nitric acid, sulfuric acid, ethyl alcohol, isobutyl alcohol, methyl alcohol, n-butyl alcohol propyl alcohol, ammonium hydroxide, aniline, aqua regia, benzaldehyde, benzene, carbon tetrachloride, caustic soda (NaOH), chlorobenzene, chloroform, cyclohexane, esters, ether, diethyl ether, isopropyl ether, methyl ethyl, hexane, hydrazine, hydrogen peroxide, methylene chloride, petroleum ether, phenol, sodium hydroxide, tetrahydrofuran, toluene, trichloroethylene, trimethylpentane, xylene, and mixtures thereof.

Moreover, the dissolvable materials can be dissolvable by any suitable technique, not just by using a solvent. For example, in some embodiments, the dissolvable material is dissolved by one of: mechanical vibration (e.g. via sonication); using electromagnetic waves; melting; and mixtures thereof. In a number of embodiments, the dissolution of the dissolvable material forms a cavity, within which an additive material can be inserted.

The process 100 further includes introducing 104 an additive material that is formed within the subassembly. The cavity can be formed in the subassembly by any suitable technique. For example, in many embodiments, a cavity is formed either during the additive manufacturing process or by dissolving some portion of the subassembly. Thus, for example, in a number of embodiments, the subassembly includes a volume that is defined by the presence of a dissolvable material, and the dissolvable material is dissolved thereby forming the cavity. Alternatively, the subassembly can be additively manufactured so that it includes a cavity. Note that where the subassembly is additively manufactured to include a cavity, the cavity can be considered to be a volume, bearing in mind that a volume can be understood to be defined by the homogenous presence, or absence, of a distinct material. As mentioned previously, the cavity can be thought of as a 'negative space.'

An additive material can be introduced into the cavity by casting or any similar technique where a material is introduced into the cavity such that it conforms to the shape of the cavity (in this way the subassembly is acting as a mold). In many embodiments, the additive material is injected into the cavity in accordance with conventional injection molding techniques. Although, it should be clear that any suitable technique of introducing an additive material into the cavity can be implemented in accordance with embodiments of the invention. For example, the additive material can be introduced into the cavity by one of: blow molding, roto molding, expanding foam molding, and expanding bead molding. Additionally, any suitable material can be inserted into the cavity. In many embodiments, a thermoset material is cast into the cavity. In a number of embodiments, a combination of hard and soft silicon thermoset materials is cast into the cavity.

As mentioned above, in many embodiments, one of the plurality of volumes defines a shape that is to exist in the object to be fabricated. Thus, for instance, the cavity can define a shape that is to exist in the object to be fabricated. For example, when a material that is to form the object is introduced into the cavity, conforms to the shape of the cavity, and solidifies, the resulting object includes a shape defined by the cavity. In this sense, the cavity has defined a 'positive space' in the fabricated object, insofar as the volume defined by the cavity is occupied by solid material in the fabricated object.

In some embodiments, one of the plurality of volumes defines a 'negative space' in the object to be fabricated, and in this way defines a shape that is to exist in the fabricated object. For example, in some embodiments, a volume in the subassembly is defined by the presence of dissolvable material, and the dissolvable material is made to dissolve and exists as a void space with respect to the fabricated object.

Accordingly, it is seen that the plurality of volumes can define the shapes of the fabricated object, either as positive spaces or negative spaces.

The process 100 further includes dissolving 106 at least one dissolvable material; the dissolving 106 can be achieved using any suitable technique. For example, the above-described solvents can be used to dissolve respective dissolvable materials. In a number of embodiments the dissolvable material is dissolved thermally (e.g. melting); in some embodiments the dissolvable material is dissolved mechanically (e.g. causing the material to vibrate at its resonant frequency until it disintegrates, for example by sonication); in some embodiments, the dissolvable material is subjected to an electromagnetic wave that causes the dissolution of the dissolvable material. Of course, any suitable technique for removing the dissolvable material can be implemented in accordance with embodiments of the invention. Moreover, in many instances, the dissolving technique is selected such that it does not cause the dissolution of at least one other material in the subassembly. For instance, in some embodiments, at least two of the volumes within the subassembly are each fabricated from distinct dissolvable materials, and a technique that is used to dissolve the first dissolvable material does not cause the dissolution of the second dissolvable material. In this way, specific volumes within the subassembly can be vacated independently during a build-up portion of the fabrication process. These techniques can be used to form unique geometries that include materials that may not easily lend themselves to conventional additive manufacturing processes.

Figure 2:
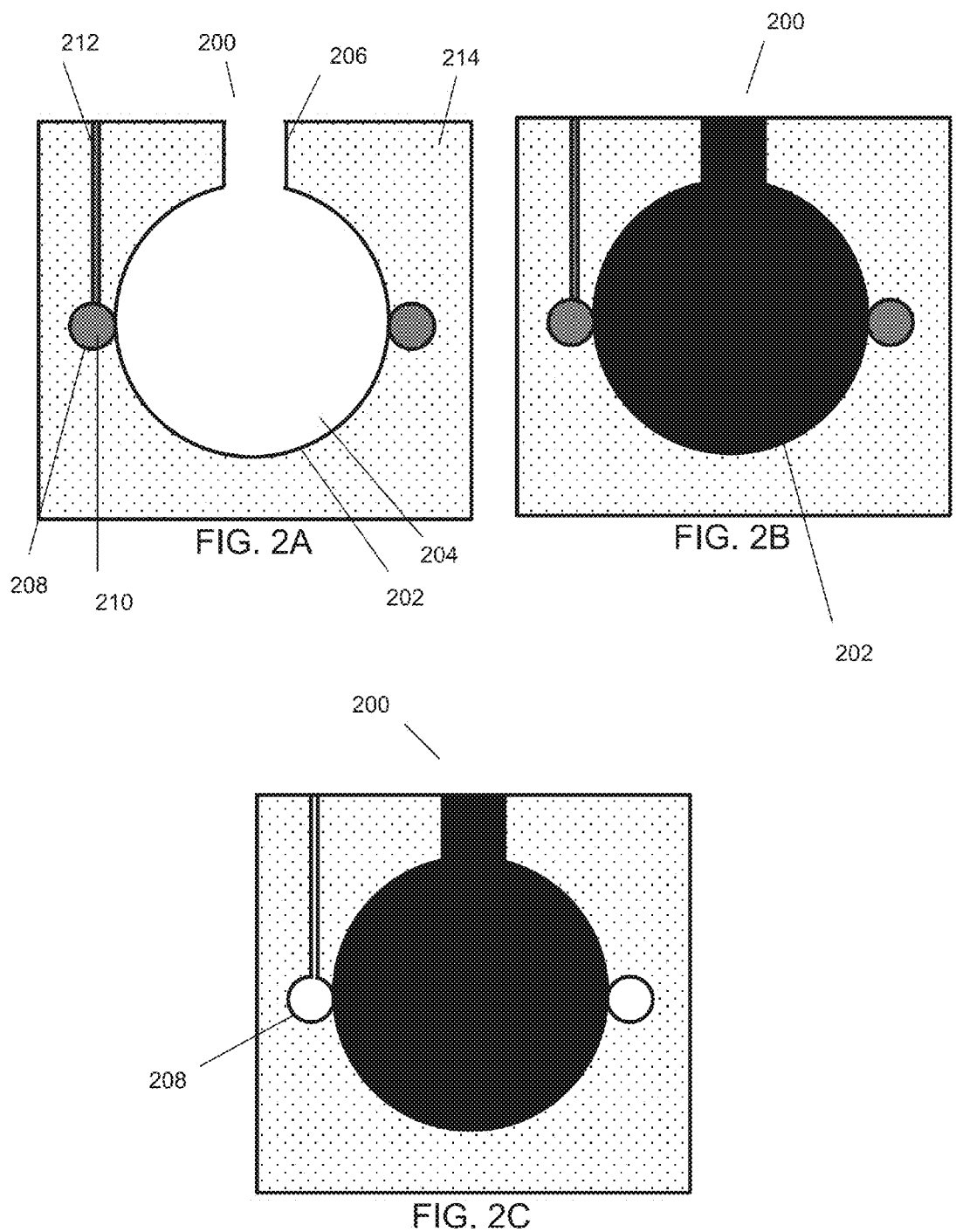
FIGS. 2A-2C illustrate the fabrication of a component in accordance with the process illustrated in FIG. 1 in accordance with embodiments of the invention.

FIGS. 2A-2C illustrate the fabrication of an exemplary object according the process outlined in FIG. 1 in accordance with embodiments of the invention. In particular, FIG. 2A depicts the cross-section of a subassembly 200 that includes a first volume 202 that has a body portion 204 and a sprue portion 206; a second volume 208 that itself includes a body portion 210 and a sprue portion 212; and a third volume. As one of ordinary skill in the art would appreciate, a sprue portion typically acts to facilitate the introduction of material into a volume. Although any shapes may be chosen for the relevant volumes, in the specific embodiment shown in FIGS. 2A-2C, the arrangement of the first volume 202, the second volume 208, and the third volume 214 is akin to a sphere (defined by the first volume 202) within a rectangular prism (defined by the third volume 214), the sphere being surrounded by a tube (defined by the second volume 208). In the illustrated embodiment, the first volume 202 is defined by the homogenous absence of material. Accordingly the first volume 202 essentially defines a cavity in the shape of a sphere. The second volume 208 is defined by the homogenous presence of a first dissolvable material. Note that second volume 208 includes a sprue portion 212 that is configured such that the body portion in connection with the sprue portions can be accessed, e.g. so that the dissolvable material can be dissolved and so that a material can be inserted into the cavity that is thereafter created, if desired.

FIG. 2B depicts the cross-section of the subassembly after the insertion of a material into the first volume 202. The material is inserted to the extent that it conforms entirely to the shape of the first volume. In some embodiments, the material is inserted to a lesser extent. It should be understood that any suitable material can be inserted into the cavity within the subassembly 200. For example, in many embodiments a thermoset material is so inserted. Additionally, the insertion can be achieved by any suitable means. In a number of embodiments, the material is injected into the cavity.

FIG. 2C depicts the object after the dissolvable material within the subassembly has been dissolved, and removed from the second volume 208. As mentioned above, the dissolution can be achieved by any suitable technique. Note that in the illustration, it is depicted that the dissolution of the dissolvable material did not impact the other volumes. Additionally, the third volume 214 acts to support the other volumes during the build-up aspect of the manufacturing technique. In this way, the spatial relationships within the additively manufactured subassembly are preserved. Accordingly, the third volume can be thought of as a tool that supports the build up of the other volumes. Generally, the finally formed object can be described as a sphere of a first material (inserted) within a rectangular prism of another material (additively manufactured), the sphere having a hollow circular tube (dissolved) around its circumference. It should of course be understood that the above descriptions are simply meant to be illustrative, and not comprehensive of the techniques described herein. For example, subassemblies of any of a variety of geometries, and including any number of volumes, can be implemented and used to build up any of a variety of fabricated objects in accordance with embodiments of the invention.

In general, with the described techniques, additive manufacturing can be used to establish a template by which a final object is fabricated. Of course it should be understood that additive manufacturing techniques and casting-like techniques can be used in tandem in a variety of ways in accordance with embodiments of the invention. For example, although the above described processes have referred to the introduction of an additive material into a cavity prior to the dissolution of a first dissolvable material, it should be clear that embodiments of invention are not necessarily so limited. Indeed, in numerous embodiments, a first dissolvable material is dissolved prior to the introduction of an additive material into a cavity. Additionally, in many embodiments, the subassembly is additively manufactured to include dissolvable materials, that can be iteratively dissolved and replaced with additive materials, and this aspect is now discussed.

Dissolving and Replacing Materials within a Subassembly

In many embodiments, a subassembly that includes a dissolvable material is additively manufactured, and the dissolvable material is made to dissolve and replaced with another material. In many embodiments, the replacing material is the material of the final object. In numerous embodiments, subassemblies are additively manufactured to include multiple dissolvable materials, and the process of dissolving the dissolvable materials and replacing them with another material is iterated as desired. In many embodiments, the dissolvable materials are made to dissolve without disturbing other dissolvable materials. These aspects can allow a more nuanced object comprising many different features and/or materials to be fabricated.

Figure 3:
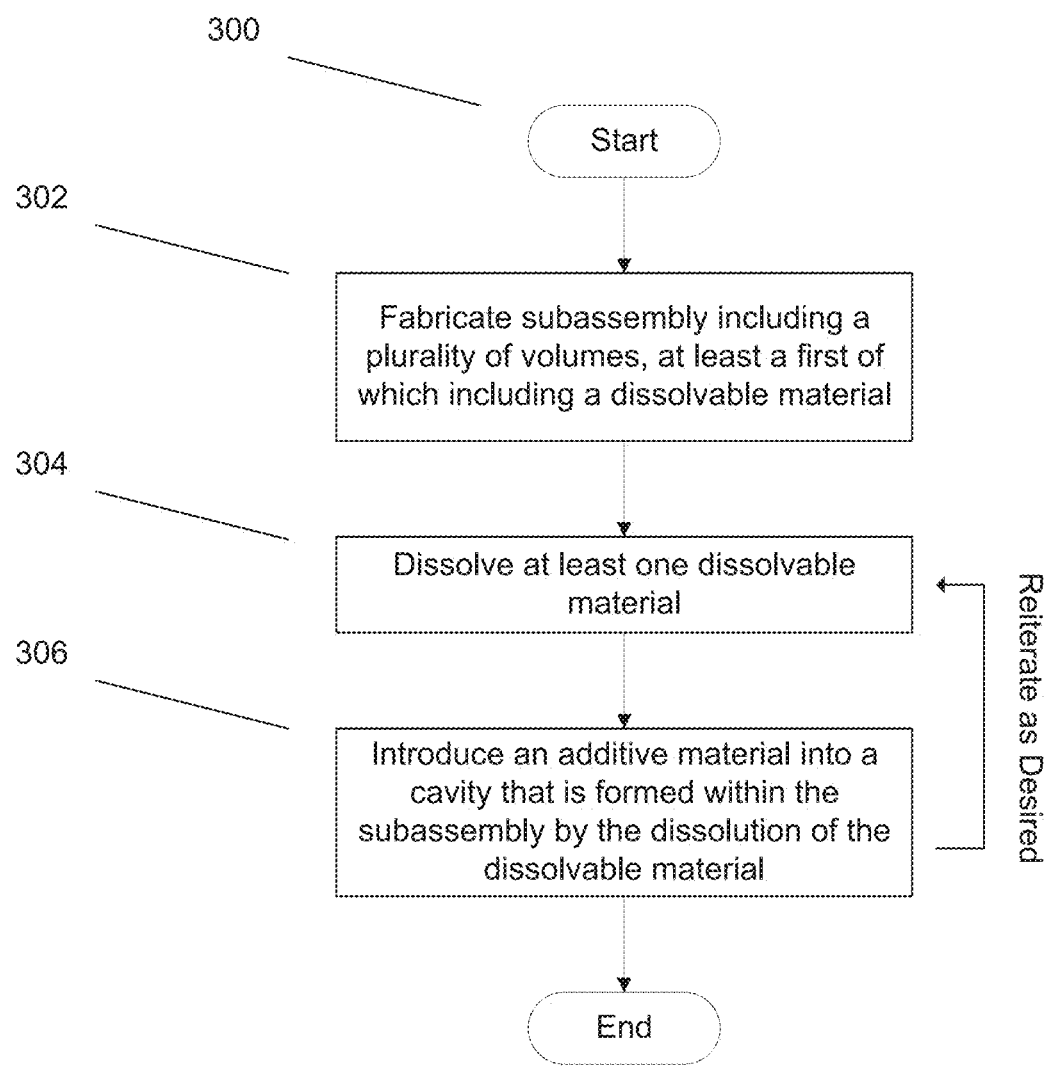
FIG. 3 illustrates a process for fabricating components using additive manufacturing techniques whereby a first inserted material is inserted into a cavity created by the dissolution of a dissolvable material that was deposited by additive manufacturing in accordance with embodiments of the invention.

FIG. 3 illustrates a process for fabricating an object that employs additively manufacturing a subassembly including a dissolvable material, and thereafter replacing the dissolvable materials with an inserted material. In particular, the process 300 includes 302 fabricating a subassembly including a plurality of volumes, where at least one of the plurality of volumes includes a dissolvable material. Although the illustration mentions a (singular) dissolvable material, in many embodiments, the subassembly can be made to include multiple volumes, each including a dissolvable material. Moreover, in numerous embodiments, the dissolvable materials are different and can be made to dissolve by techniques that would not dissolve at least one other dissolvable material. Additionally, as mentioned before, in many embodiments, the volumes are configured to define shapes that are to exist in the final object. For example, as mentioned above, the volumes can define positive spaces in the fabricated object or negative spaces in the fabricated object.

The process 300 further includes dissolving 304 a dissolvable material in the subassembly. As discussed previously, the dissolvable material can be made to dissolve using any suitable technique including e.g., thermally, mechanically, chemically, and via electromagnetic radiation. As can be inferred, in many embodiments, dissolving the dissolvable material is accomplished using a technique that does not dissolve any other material in the subassembly.

The dissolution 304 of the dissolvable material thereby creates a cavity in the subassembly. Accordingly, the process further includes introducing 306 an additive material into the cavity created by the dissolution of the dissolvable material. As before, the material can be inserted into the cavity in any suitable manner in accordance with embodiments of the invention, including by casting or any other similar procedure.

Note that the illustration indicates that the processes of dissolving 304 and inserting 306 can be iterated as desired. For example, where a subassembly includes multiple volumes each having a dissolvable material, the aspects of dissolving the respective dissolvable materials and replacing them with introduced additive materials can be iterated for each of the dissolvable materials. In these instances, the dissolving techniques can be selected such that they do not adversely impact the other materials in the subassembly. Although in some embodiments, at least two volumes within the subassembly include the same dissolvable material; in this way, the volumes can be vacated simultaneously if desired. Additionally, as can be appreciated from the discussion above, although the illustrated embodiment depicts that a dissolvable material is dissolved as prior the introduction of an additive material into a cavity—it should be clear that embodiments of the invention are not so limited; in many embodiments, an additive material is introduced into a cavity prior to the dissolution of a dissolvable material within the subassembly.

Figure 4A:
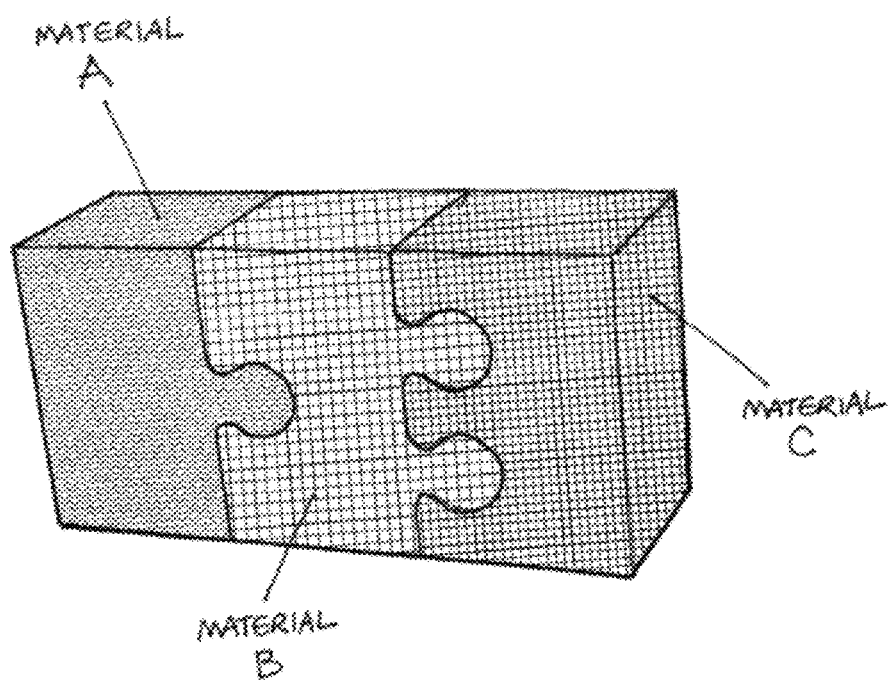
Figure 4B:
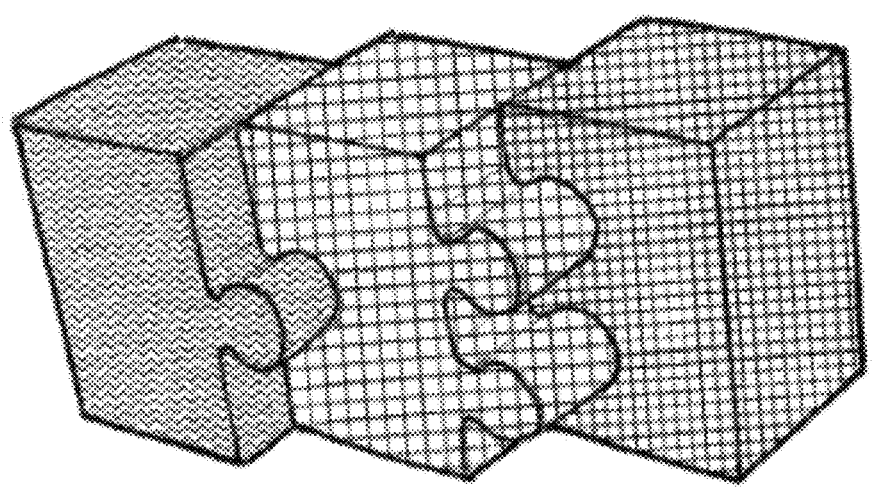

FIGS. 4A-4L illustrate how the process described above with respect to FIG. 3 may operate. In particular, FIG. 4A depicts a unique geometry that is to be fabricated, that includes Material A, Material B, and Material C. Generally, the geometry in FIG. 4A can be described as a rectangular prism including three materials, where the materials exist within the rectangular prism in the shape of jigsaw puzzle pieces. FIG. 4B depicts an exploded view of the geometry seen in FIG. 4A, and illustrates the materials having the shapes of jigsaw puzzle pieces.

Figure 4C:
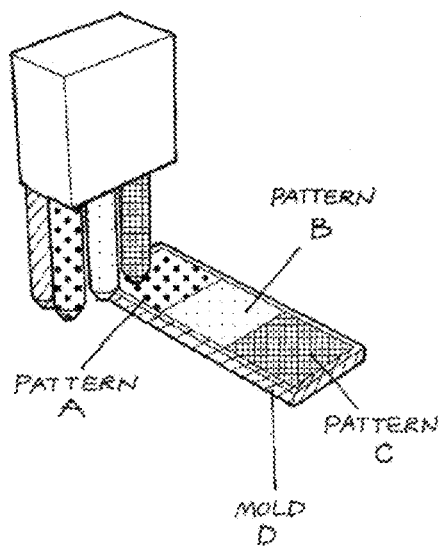
Figure 4D:
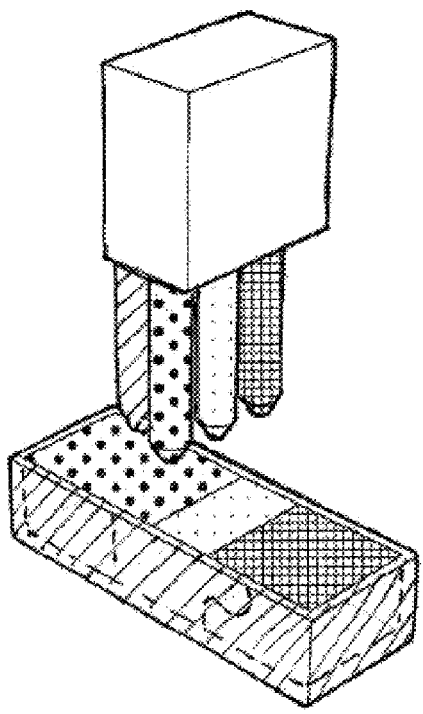
Figure 4E:
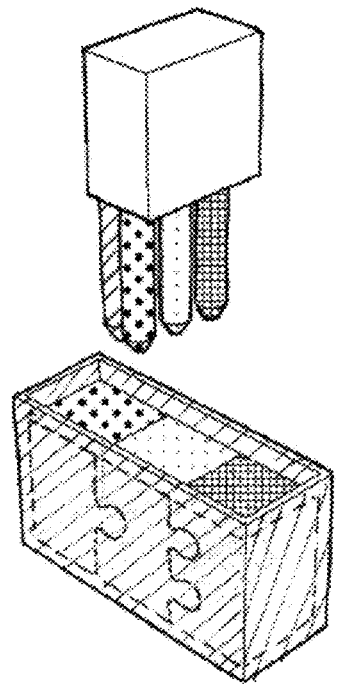
Figure 4F:
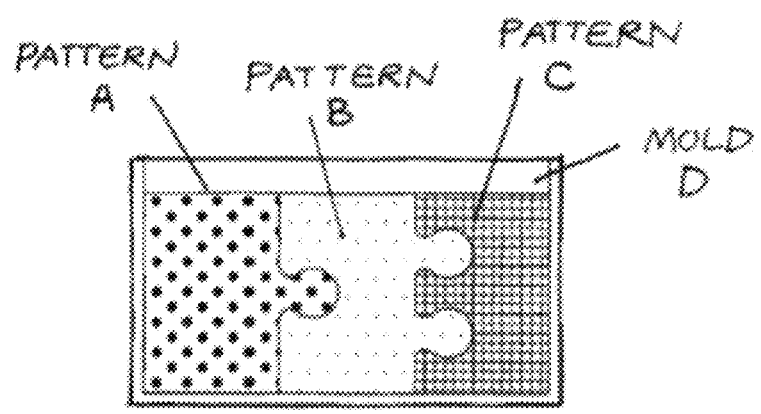

FIGS. 4C-4E depict the additive manufacturing of the subassembly that can be implemented in the process. In particular, the subassembly is additively manufactured to define three patterns—Pattern A, Pattern B, and Pattern C—and a mold—Mold D. Each of the patterns is defined by the presence of a unique dissolvable material, and each pattern defines the shape of a respective material (i.e. Material A, Material B, and Material C) as it is to exist in the fabricated object. Each of the dissolvable materials can be made to dissolve using a technique that would dissolve other dissolvable materials within the subassembly or other introduced additive materials. FIG. 4F illustrates a cross-section of the sub-assembly that is additively manufactured.

Figure 4G:
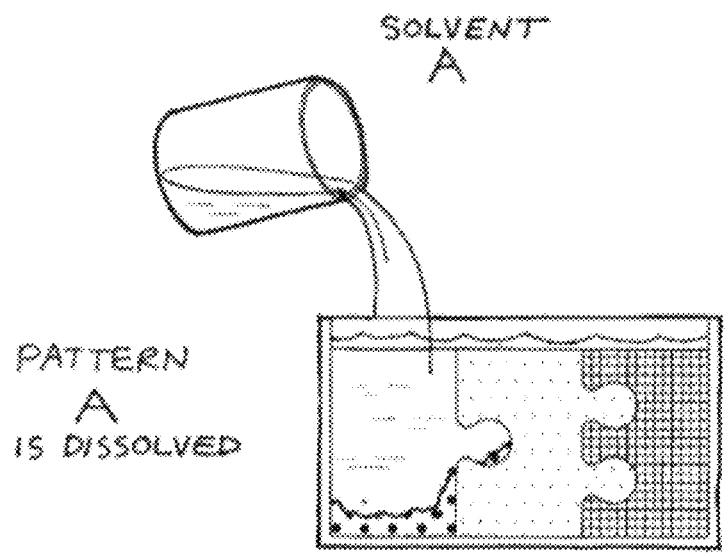
Figure 4H:
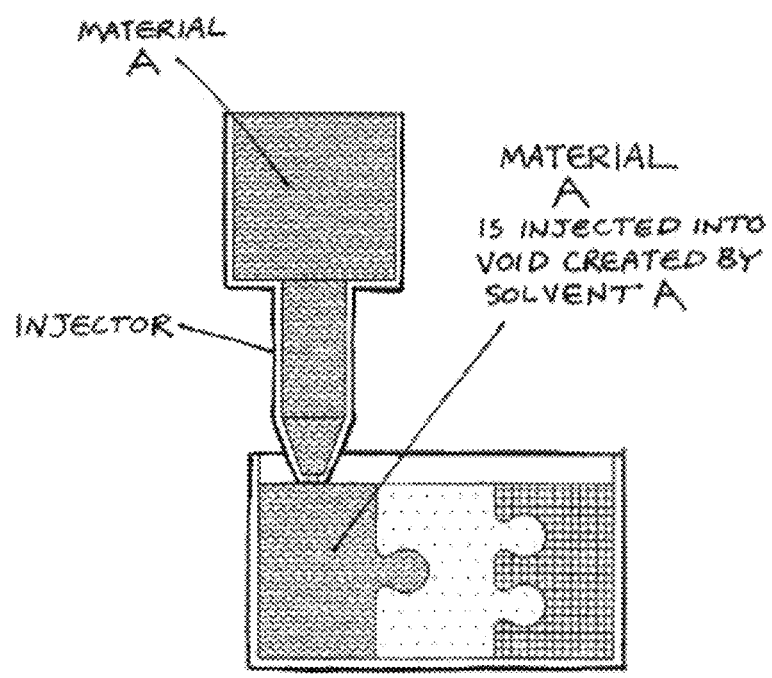

FIG. 4G illustrates the dissolution of the dissolvable material that defines Pattern A. In the illustrated embodiment, the dissolution is accomplished using a solvent. Note that the solvent does not dissolve either of the dissolvable materials that define Pattern B and Pattern C. The solvent and the disintegrated material are subsequently removed. In this way, Pattern A can be said to be preserved insofar as Pattern A is now defined by the homogenous absence of material. FIG. 4H illustrates the insertion of Material A into the volume that is Pattern A, now made to be a void by the dissolution of the dissolvable material of Pattern A. Material A can be any suitable material including a material that would not be suitable for conventional additive manufacturing processes. In the illustrated embodiment, the insertion is achieved by an injector, but it should be understood that the insertion can be achieved using any suitable technique in accordance with embodiments of the invention. Material A can then be allowed to solidify.

FIGS. 4I-4J depict the same processes as those seen in FIGS. 4G-4H, but with respect to the dissolvable material of Pattern B and Material B. Note that the solvent that is used to dissolve Pattern B does not dissolve either the dissolvable material of Pattern C or Material A.

Figure 4K:
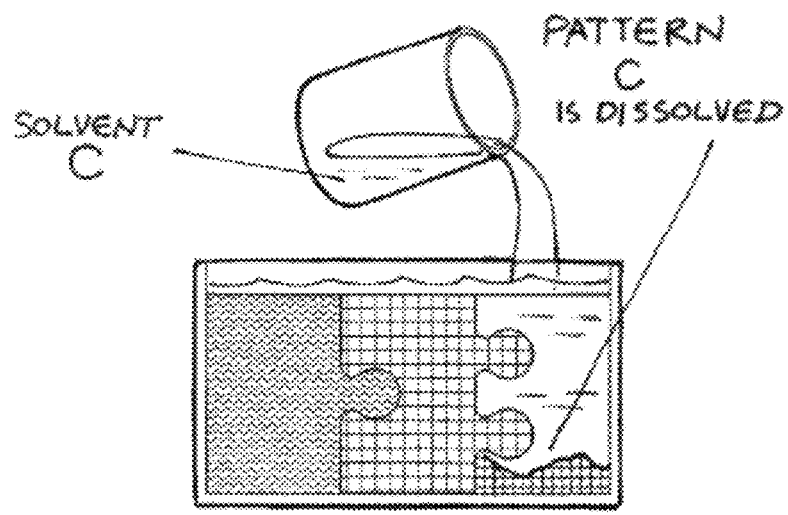
Figure 4L:
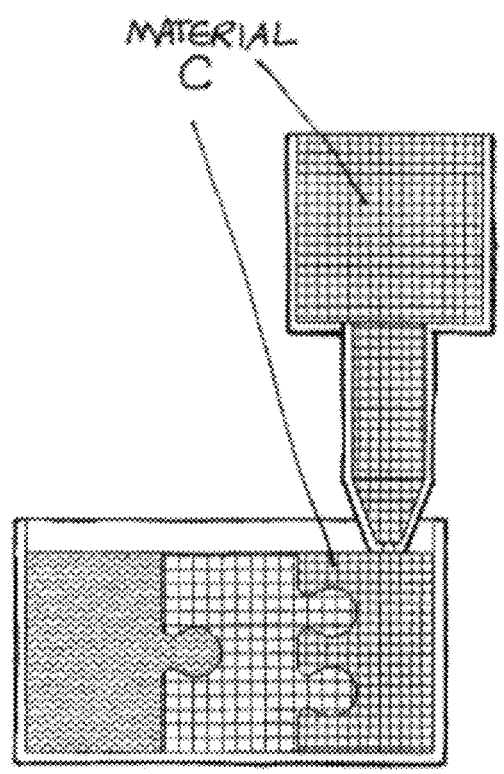

FIGS. 4K-4L depict the same processes as those seen in FIGS. 4G-4H and 4I-4J, but with respect to Pattern C and Material C. Again, the solvent used to dissolve the dissolvable material of Pattern C does not disrupt the other materials in the partially built up subassembly.

When Material C solidifies, the desired object as seen in FIG. 4A can be removed from the mold by any suitable technique in accordance with embodiments of the invention. For example, the object can be removed mechanically; the object can also be removed by dissolving the mold. As can be appreciated, the mold can be dissolved using a technique that does not adversely affect Material A, Material B, or Material C. Thus, it can be seen that, using the described techniques, additive manufacturing processes can be used to fabricate an object from materials that may not easily lend themselves to additive manufacturing processes.

Figure 5A:
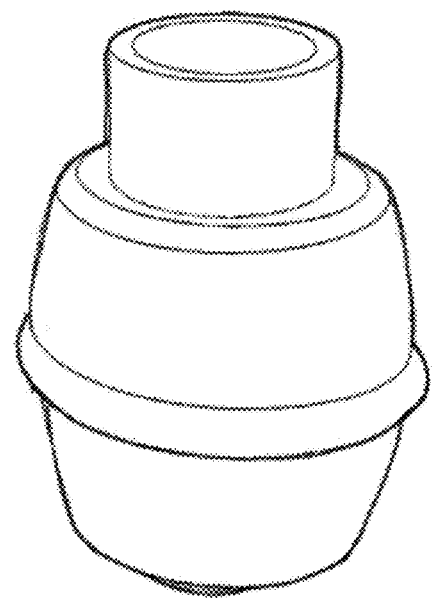
Figure 5B:
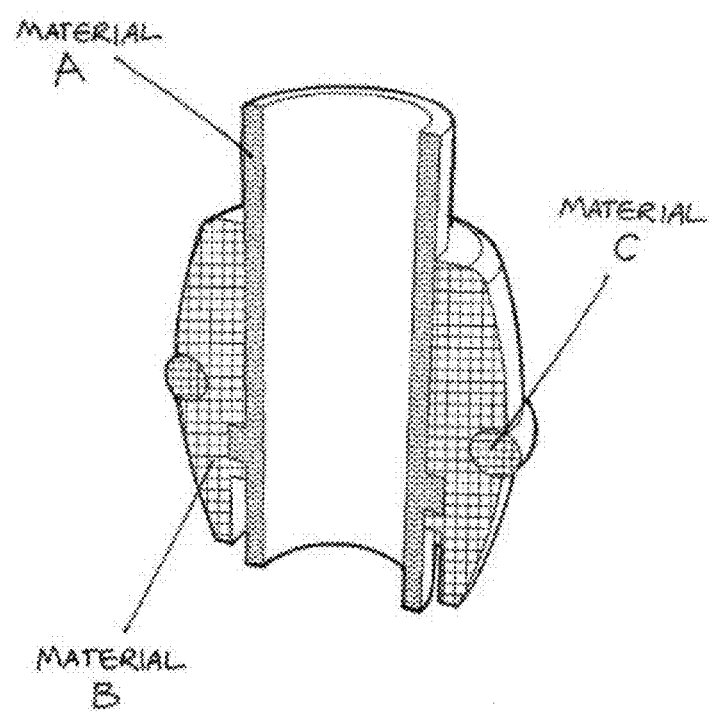

FIGS. 5A-5L illustrate how the process depicted in FIG. 3 can be used to fabricate a continuous positive airway pressure (CPAP) coupling in accordance with embodiments of the invention. In particular, FIG. 5A illustrates the CPAP coupling that can be fabricated, and FIG. 5B illustrates a cross-section of the coupling. The CPAP coupling includes a passageway that is made from Material A; a housing made from Material B; and a circumferential band made from Material C.

FIGS. 5C-5E illustrate the additive manufacturing of the subassembly. In particular, the subassembly is shown to be additively manufactured to include a mold, Pattern A, Pattern B, and Pattern C. Each of Pattern A, Pattern B, Pattern C, and the mold includes a dissolvable material. Pattern A defines the passageway; Pattern B defines the housing; Pattern C defines the circumferential band; and Pattern D defines the mold.

Figure 5F:
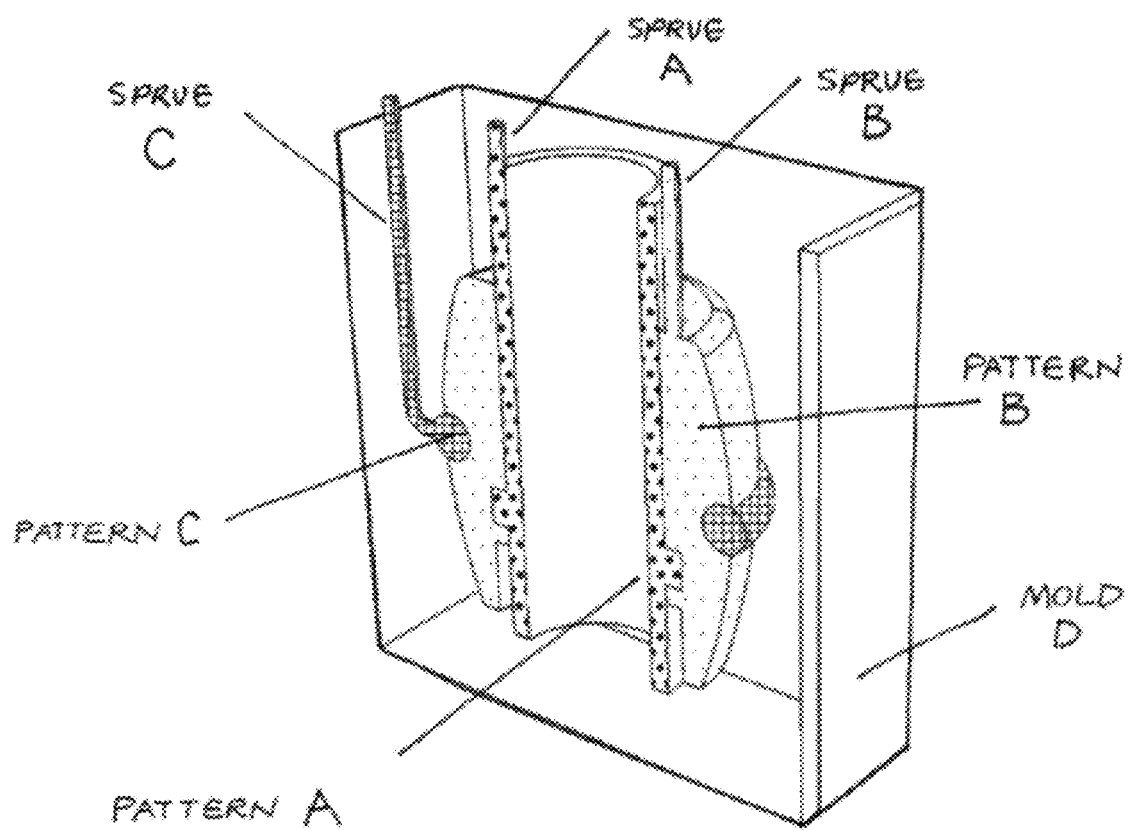

FIG. 5F illustrates a cross-section of the subassembly after it has been additively manufactured. Note that each of Pattern A, Pattern B, and Pattern C, includes a sprue portion that can facilitate the insertion of a material (e.g. via casting). Typically, a sprue portion extends from a body to an external surface, and is thereby accessible. In some embodiments, a sprue portion can include a dissolvable material such that when it is no longer needed in the build-up process, it can be made to dissolve. Note that for purposes of simplicity, the mold is depicted as hollow.

Figure 5G:
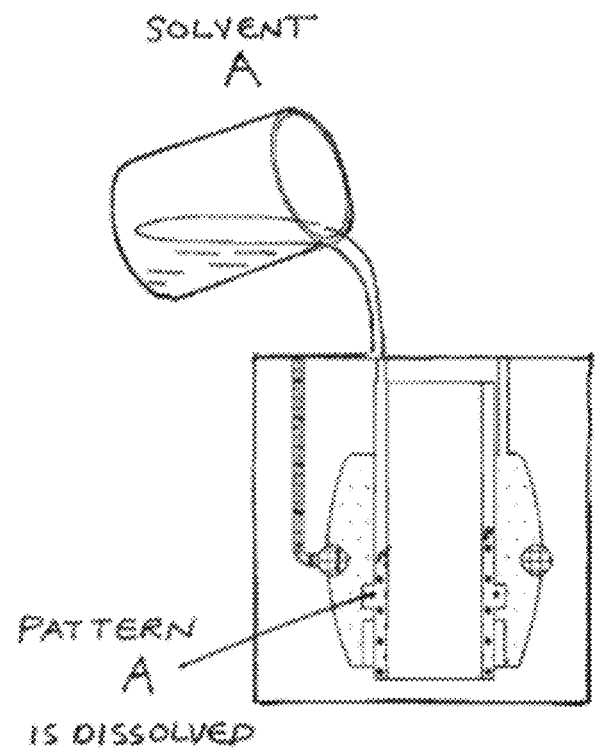
Figure 5H:
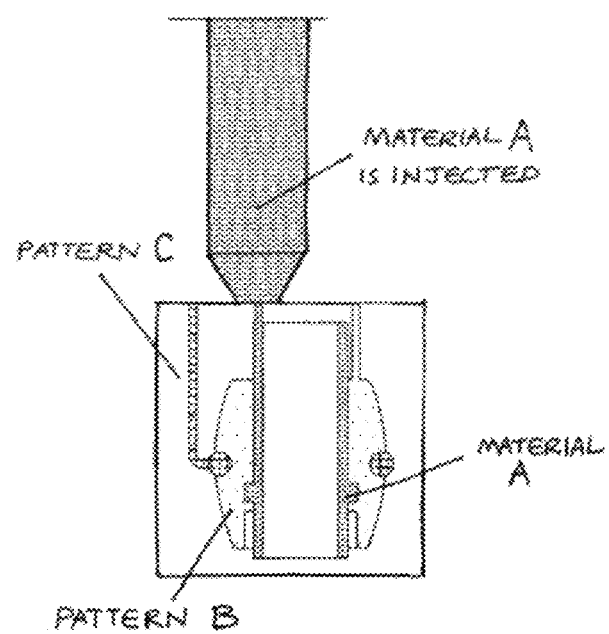
Figure 5I:
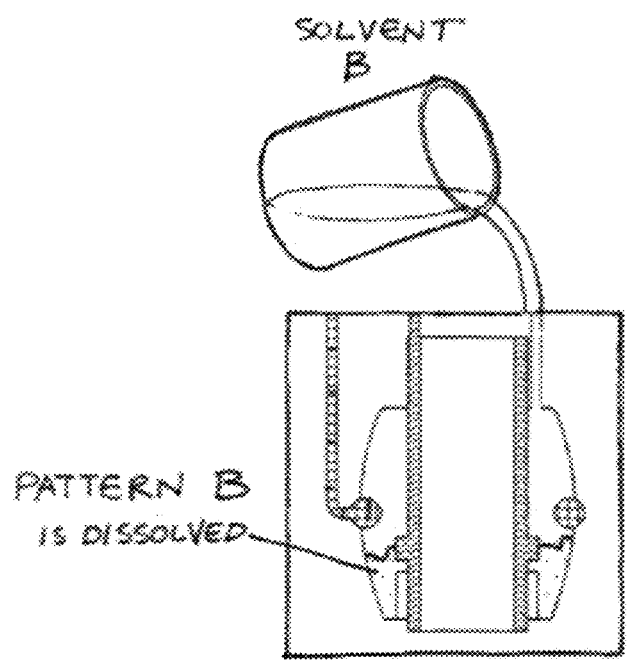
Figure 5J:
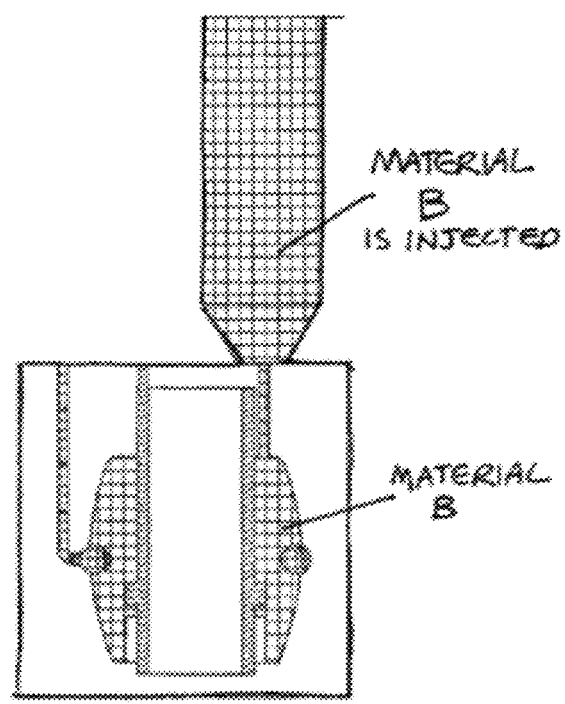
Figure 5K:
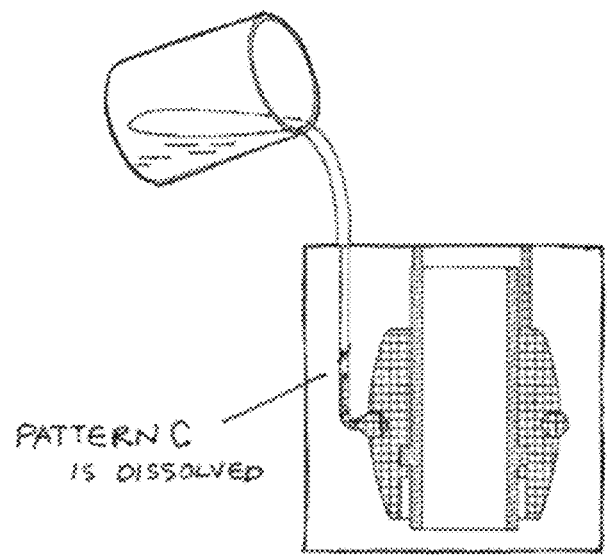
Figure 5L:
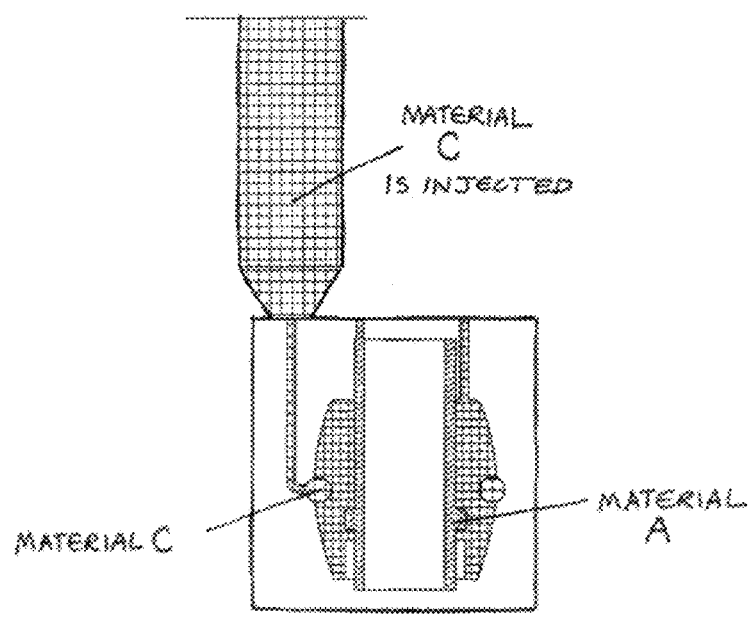

FIGS. 5G-5H depict the dissolution of the dissolvable material of Pattern A, and the subsequent insertion of Material A into the cavity created by the dissolution of the dissolvable material of Pattern A. Note that the sprue portion is used to facilitate the insertion of the material. Also, the dissolution of materials within the subassembly is accomplished using a technique that does not disturb the integrity of the other materials within the subassembly. FIGS. 5I-5J illustrate the same processes as that seen with respect to FIGS. 5G-5H with respect to the dissolvable material of Pattern B and Material B. Similarly, FIGS. 5K-5L illustrate the same processes as those seen with respect to FIGS. 5G-5H and 5I-5J with respect to the dissolvable material of Pattern C and Material C.

As before, after the inserted materials have solidified, the CPAP coupling can be removed from the mold using any suitable technique. Thereafter, any undesired sprue portions can be removed, and the CPAP coupling as depicted in FIG. 5A can be obtained.

Figure 6A:
FIGS. 6A-6G illustrate the fabrication of a shoe, whereby a predetermined arrangement of patterns is additively manufactured using dissolvable materials, and the dissolvable materials are subsequently dissolved and replaced by materials that constitute the component to be fabricated in accordance with embodiments of the invention.
Figure 6B:
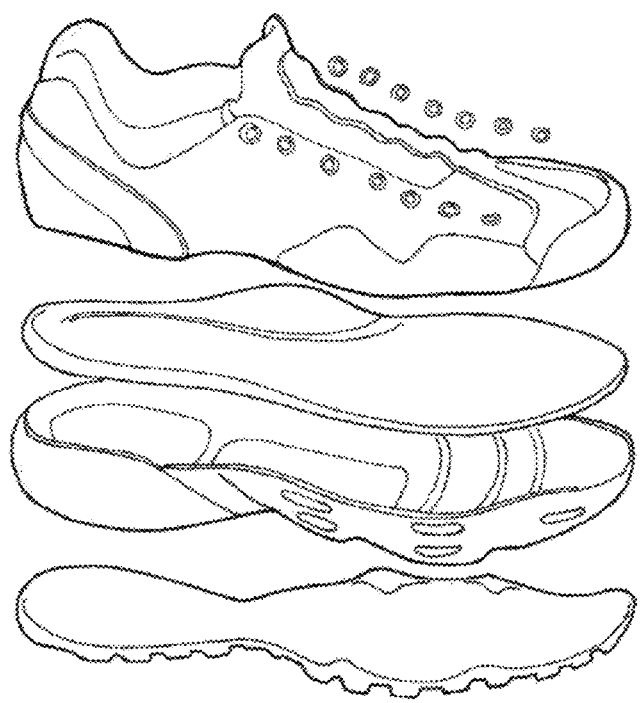

Of course, it should be understood that these processes can be used to create any of a variety of objects in accordance with embodiments of the invention, not just couplings. For example, FIGS. 6A-6G illustrate how a shoe may be fabricated using the process depicted in FIG. 3. In particular, FIG. 6A depicts a shoe that can be made, and FIG. 6B depicts an exploded view of the shoe that can be made. As before, a sub-assembly is additively manufactured that includes patterns that define the shape of the shoe. The patterns can further include sprue portions that can facilitate the insertion of materials into the created cavities. Also, as before, the patterns made of dissolvable materials can be iteratively dissolved and replaced with inserted materials.

Figure 6C:
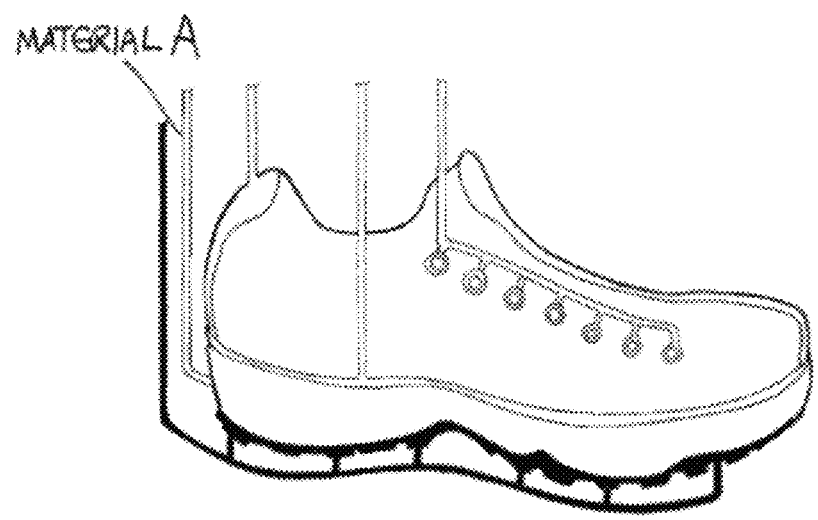
Figure 6D:
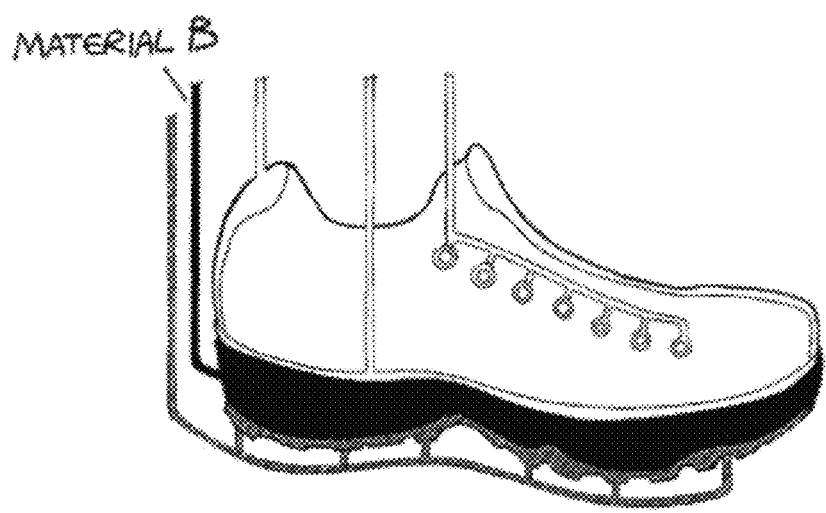
Figure 6E:
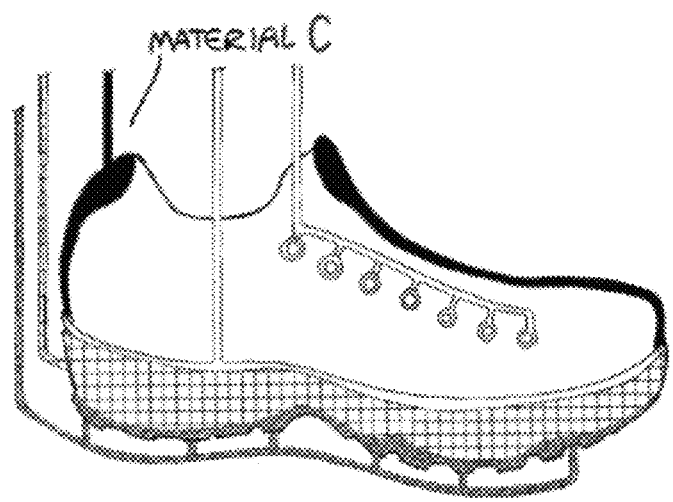
Figure 6F:
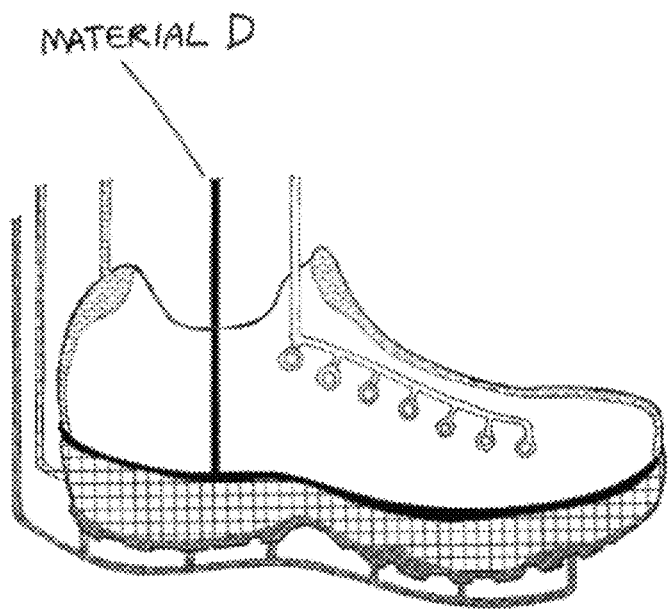
Figure 6G:
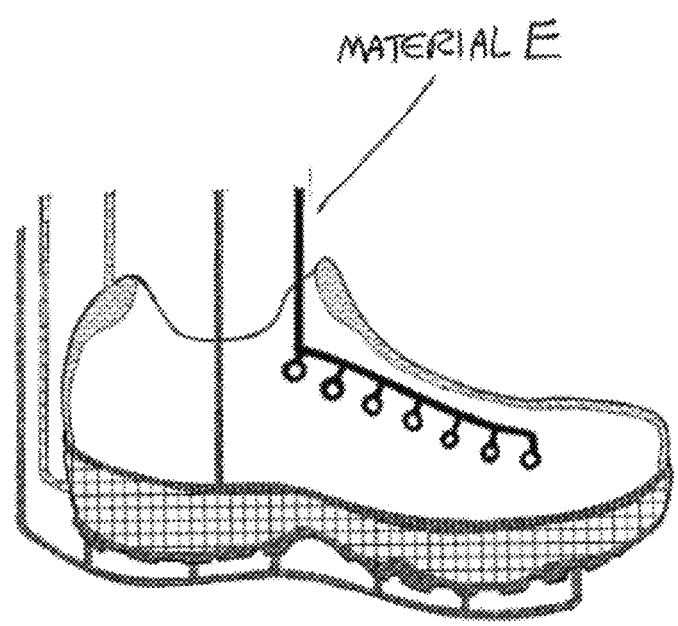

In particular, FIG. 6C illustrates the insertion of Material A into a first cavity that defines the tread of the shoe; FIG. 6D illustrates the insertion of Material B into a second cavity that is formed within the subassembly that defines the sole of shoe; FIG. 6E illustrates the insertion of Material C into a third cavity that is formed within the subassembly that defines the upper of the shoe; FIG. 6F illustrates the insertion of a Material D into a fourth cavity that is formed within the subassembly that defines the padding of the shoe; and FIG. 6G illustrates the insertion of a Material E into a fifth cavity that is formed within the subassembly that defines the lace grommets of the shoe.

Accordingly, it should be appreciated that the described techniques can be used to fabricate any of a variety of objects in accordance with embodiments of the invention. While the above-description has focused on particular fabrication processes, in many embodiments of the invention, the subassemblies are additively manufactured to include particular supportive geometries that can facilitate the build up of the object to be fabricated, and this aspect is now discussed.

Geometries within Subassemblies that Facilitate the Insertion of Materials and Support Spatial Relationships During Build Up In many embodiments, the subassembly is made to include a cavity, such that when a material is cast into the cavity, the solidified material acts as a structural support to maintain the spatial relationship of two volumes within the subassembly, for example, to withstand any further dissolution procedures. A material that temporarily supports the spatial relationship of two volumes within a subassembly during the fabrication process can be understood to be a 'buck.' In many embodiments, the cavity includes a sprue portion that can facilitate the insertion of material into the subassembly.

Figure 7:
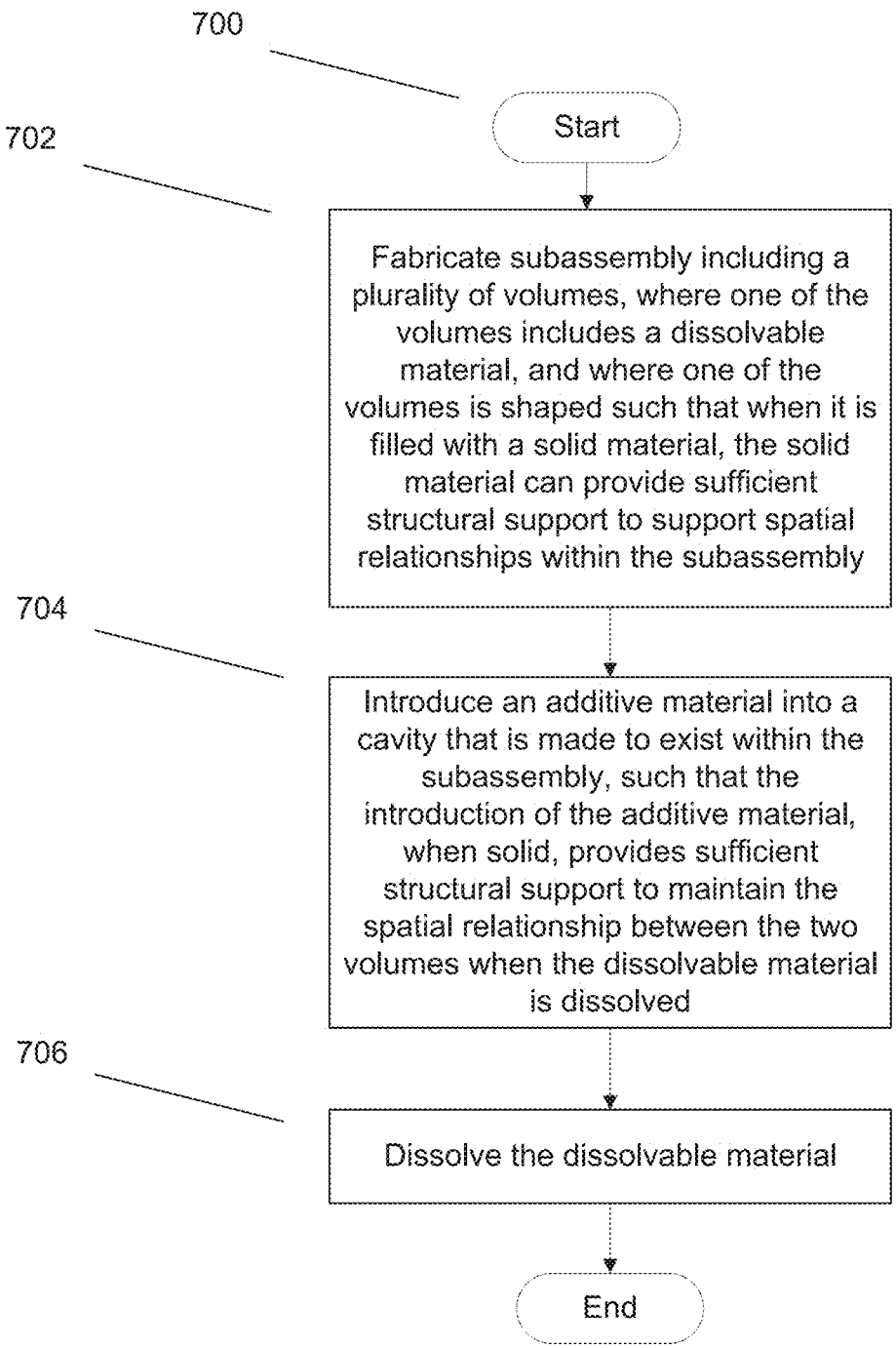
FIG. 7 illustrates a process for fabricating components using additive manufacturing techniques, whereby the spatial relationship between two volumes is preserved during the post-additive manufacturing build-up of the component in accordance with embodiments of the invention.

FIG. 7 illustrates a process for fabricating an object, whereby the subassembly includes a volume that is shaped such that when it is filled with a solid material, the solid material can provide sufficient structural support to maintain the spatial relationship between two volumes within the subassembly. In particular, the process 700 includes fabricating 702 a subassembly including a plurality of volumes, where one of the volumes includes a dissolvable material, and where one of the volumes is shaped such that when it is filled with a solid material beyond a certain extent, the solid material can provide sufficient structural support to maintain spatial relationships within the subassembly (e.g. during subsequent dissolution procedures). In many embodiments, the subassembly includes a volume that defines a sprue portion, and the sprue portion when filled with a solid material beyond a certain extent can provide the aforementioned sufficient structural support.

The process 700 further includes introducing 704 a material into a cavity formed within the subassembly, where the cavity is defined by the aforementioned volume that can provide structural support when filled with a solid material; the material 704 is introduced to the extent that when it solidifies, it provides sufficient structural support to maintain the spatial relationship between two volumes, for example even when the dissolvable material is dissolved.

Accordingly, the process 700 further includes dissolving 706 a dissolvable material within the subassembly. As the solidified material provides sufficient structural support, the spatial relationship between two volumes within the subassembly can be maintained. This process can be used to fabricate objects that have unique geometries from materials that may not be sufficiently compatible with conventional additive manufacturing processes. For example, geometries containing inner volumes within outer volumes can be fabricated.

Figure 8A:
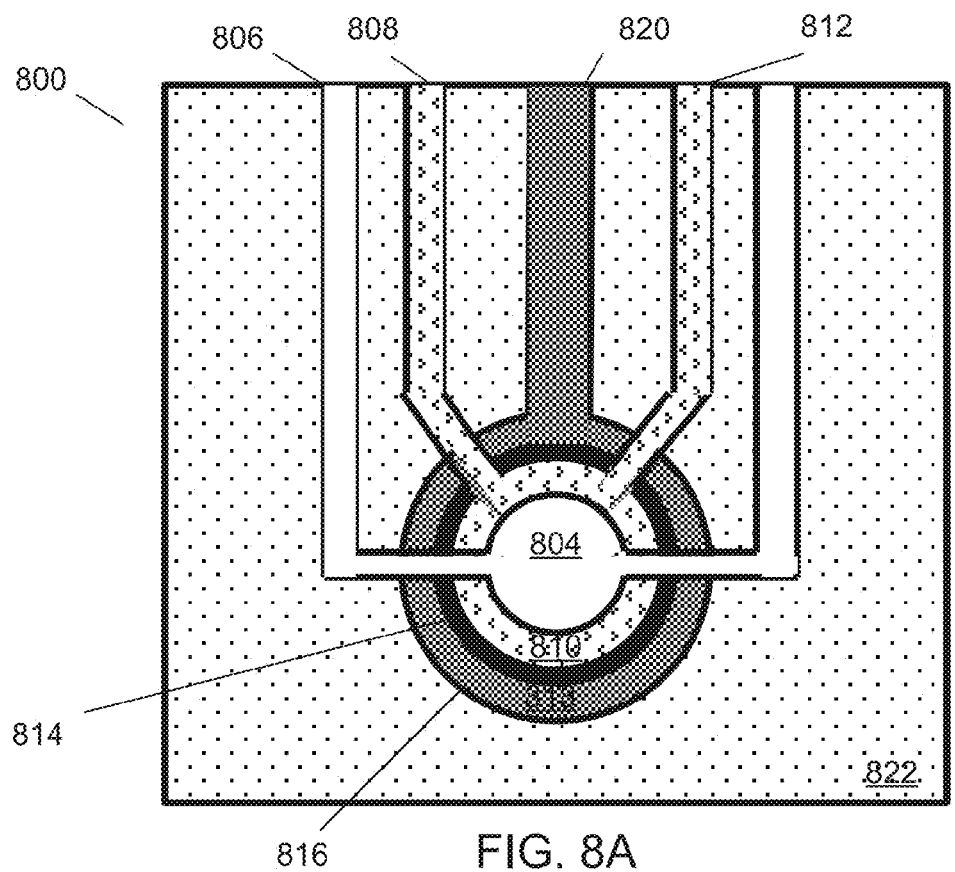
FIGS. 8A-8D illustrate the fabrication of a component, whereby the spatial relationship between two volumes is preserved during the post-additive manufacturing build-up of the component in accordance with embodiments of the invention.

FIGS. 8A-8D illustrate the fabrication of an object according to the process outlined in FIG. 7 in accordance with embodiments of the invention. In particular the illustrated object to be fabricated can be described as an inner sphere within a hollowed outer sphere, the inner sphere having rods protruding from it. More specifically, FIG. 8A depicts a cross-section of a subassembly 800 that includes a first volume 802, which itself includes a body portion 804 that is in the shape of a sphere and sprue portions 806. The sprue portions 806 extend from the body portion 804 to the surface of the subassembly. Note that, in this embodiment, the first volume 802 is hollow, i.e. defined by the homogenous absence of material. The subassembly 800 further includes a second volume 808 that also includes a body portion 810 and sprue portions 812. The body portion 810 is in the shape of a spherical shell. More specifically, the body portion of the first volume 804 is within the body portion of the second volume 810. The second volume includes a dissolvable material. The subassembly 800 further includes a third volume 814, that itself includes a non-dissolvable material (i.e. material that will not dissolved by any techniques applied during the buildup portion of the fabrication process); the third volume is in the shape of a spherical shell and envelopes the first volume 802 and the second volume 808. The subassembly 800 further includes a fourth volume 816 that also includes a body portion 818 and a sprue portion 820. The body portion 818 is in the shape of a spherical shell and envelopes the first volume 802, the second volume 808, and the third volume 814. The subassembly further includes a fifth volume 822 that houses the other four volumes. The fifth volume 822 can be understood to be a tool that supports the buildup of the object to be fabricated. Of course, it should be clear at the outset that the subassembly can be fabricated to include any of a variety of volumes, which can be of any of a variety of shapes. The illustrated embodiment is only meaning to illustrate an example of the fabrication of one particular object, and is not meaning to suggest that the geometries that can be fabricated in accordance with the described techniques are limited to those discussed.

Figure 8B:
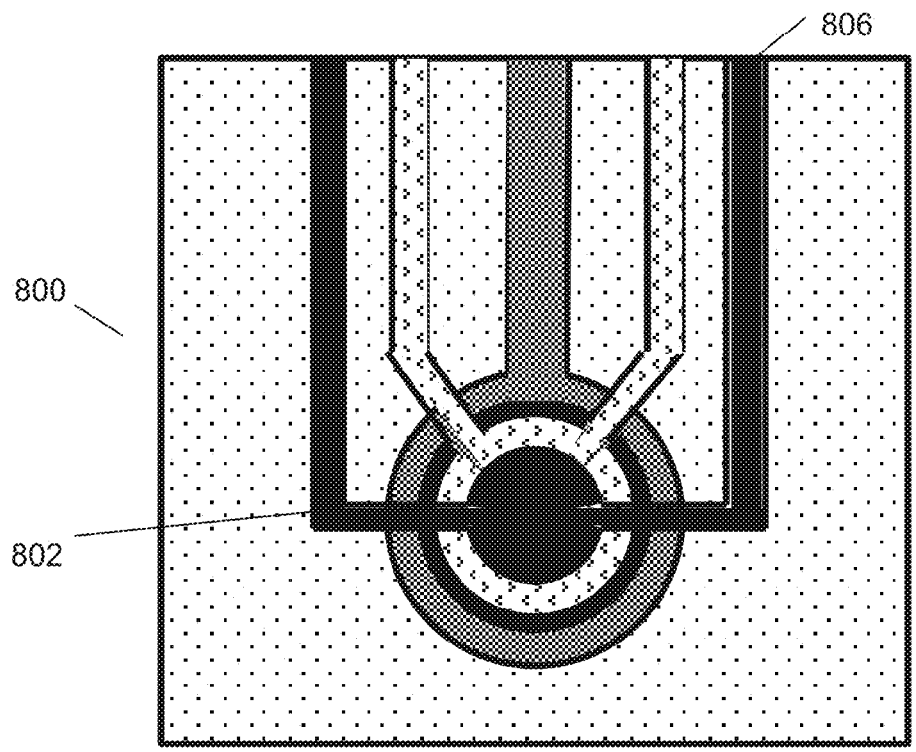

FIG. 8B illustrates the subassembly 800 after a first inserted material is inserted into the cavity that is defined by the first volume 802. The inserted material is inserted such that it extends through the sprue portions 806 and thereby fills the entirety of the first volume 802. The first inserted material can be inserted in any suitable manner in accordance with embodiments of the invention. For example, it can be injected into the first volume.

Figure 8C:
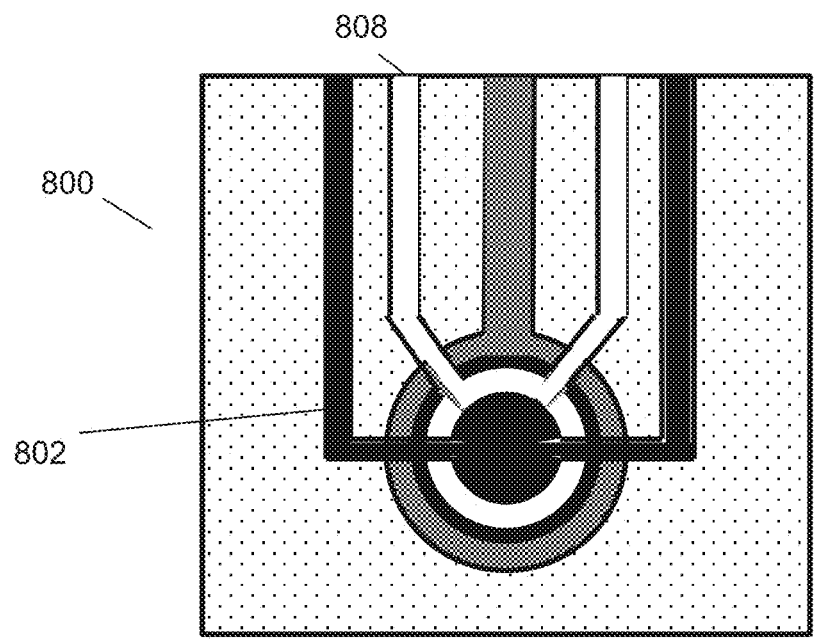

FIG. 8C illustrates the subassembly 800 after the dissolvable material in the second volume 808 has been dissolved. Note that the spatial relationship between the first volume 802 and the second volume 808 is maintained even after the dissolvable material of the second volume is dissolved.

Figure 8D:
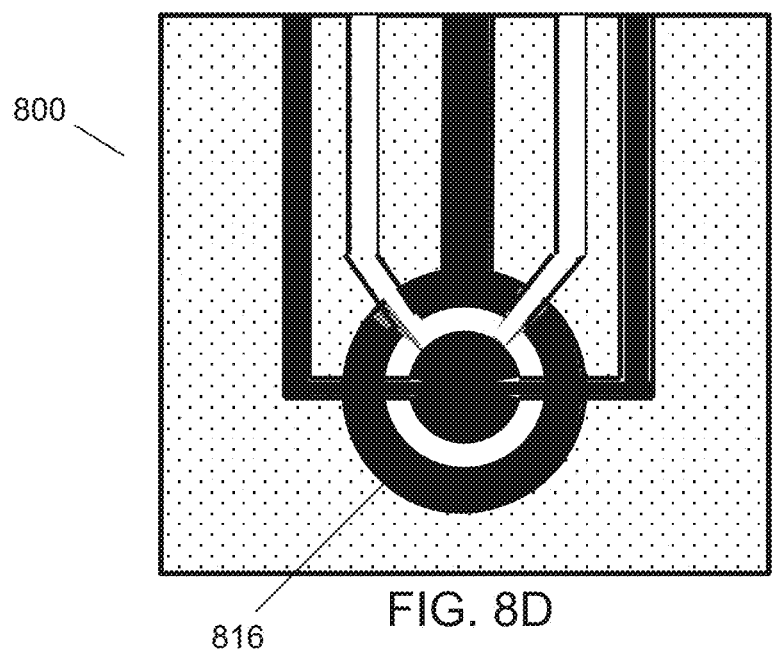

FIG. 8D illustrates the subassembly 800 after the dissolvable material of the fourth volume 816 is dissolved and replaced with a second inserted material.

Thus it is seen, how the above-described processes can be used to create unique geometries from materials that may not be compatible with conventional additive manufacturing processes. For example, while the above-discussion regarded a subassembly defining volumes within volumes, it should be understood that geometries having any number nested volumes can be created using the above processes As can be appreciated, the volumes can define either negative or positive spaces in the object to be fabricated, and the subassembly can be built up accordingly; in this way, an object that includes solid bodies within solid bodies can be defined. Of course, the supportive structures that can maintain spatial relationships within the subassembly can facilitate this result. Note that the above-discussion with respect to FIGS. 7 and 8 is not meant to be limited to the fabrication of objects having nested solid bodies; instead, the above-described processes can be used to create any of a variety of geometries in accordance with embodiments of the invention.

More generally, it should be understood that the above-descriptions are meant to be illustrative and not exhaustive. Notably, the above-described techniques can be modified in any of a variety of ways in accordance with embodiments of the invention. For example, in many embodiments, the additive materials are treated during the 'build up' phase—in some embodiments, the additive materials are colored (e.g. using a dye); in a number of embodiments, the additive materials are etched (e.g. like in a circuit board); in many embodiments, the additive material is impregnated with a chemical (e.g. a binder) for a future reaction. Of course, the additive material can be treated in any suitable way in accordance with embodiments of the invention. Note that the iterative aspect of the build-up phase can be conducive to independently treating each additive material as desired.

Figure 9:
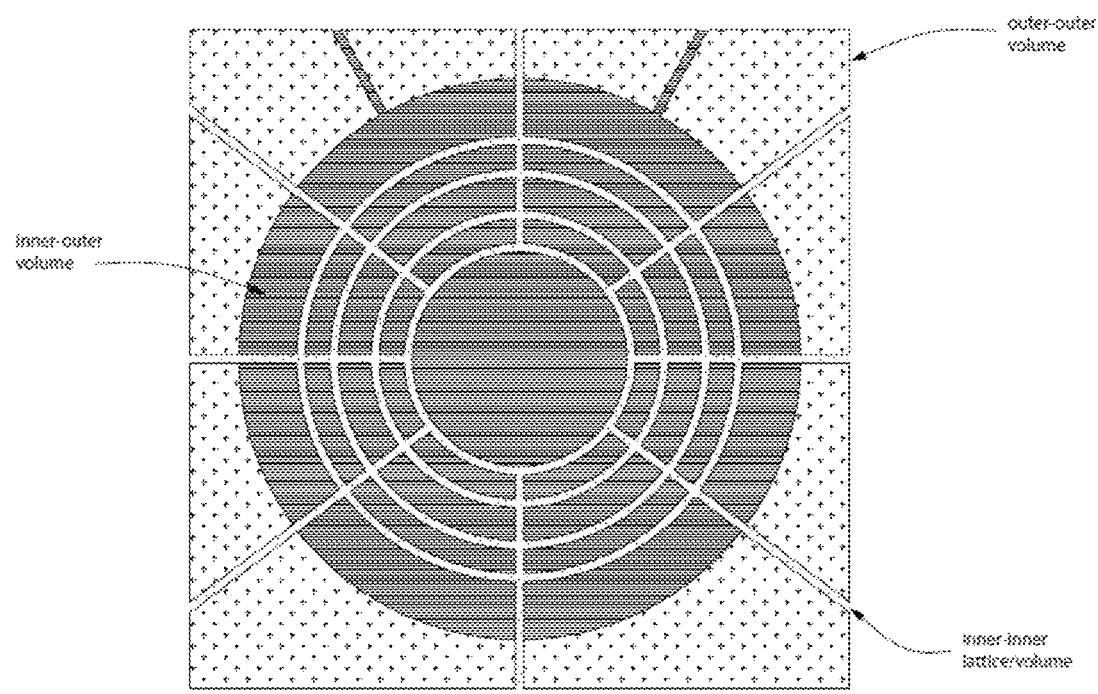
FIG. 9 illustrates the cross-section for a subassembly for the fabrication of a geometry that includes a sphere having an internal lattice structure in accordance with embodiments of the invention.

Additionally, it should be clear that any of a variety of geometries can be created in accordance with embodiments of the invention. For example, FIG. 9 illustrates a cross-section of a subassembly for an object that can be described as a sphere including an internal lattice structure that can be fabricated in accordance with embodiments of the invention. In general, as can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method of fabricating an object comprising:
fabricating a subassembly comprising a plurality of volumes;
wherein each volume is defined by the homogenous presence or absence of a material;
wherein fabricating the subassembly comprises using an additive manufacturing process;
wherein at least one of the plurality of volumes defines a shape that is to exist in the object to be fabricated;
wherein at least a first of the plurality of volumes comprises a first dissolvable material;
forming a first cavity within the subassembly;
wherein the first cavity is adjacent to the first dissolvable material;
introducing a first additive material into the first cavity;
dissolving the first dissolvable material subsequent to the introduction of the first additive material;
wherein the dissolution of the first dissolvable material does not dissolve at least one other material within the subassembly;
wherein the dissolution of the first dissolvable material results in the creation of a second cavity that is adjacent to the introduced first additive material; and
introducing a second additive material into the second cavity that is different from the first additive material.

2. The method of claim 1, wherein the subassembly is additively manufactured to include at least one cavity.

3. The method of claim 1, wherein the first cavity is formed by dissolving at least one of the plurality of volumes.

4. The method of claim 3, wherein the subassembly comprises a volume that is defined by the homogenous presence of a material, where the material acts to support the subassembly when the first cavity is formed and when the first additive material is introduced into the first cavity.

5. The method of claim 4, further comprising removing the material that acts to support the subassembly when the first cavity is formed and when the first additive material is introduced into the first cavity.

6. The method of claim 5, wherein the removal of the material that acts to support the subassembly when the first cavity is formed and when the first additive material is introduced into the first cavity is achieved mechanically.

7. The method of claim 5, wherein the removal of the material that acts to support the subassembly when the first cavity is formed and when the first additive material is introduced into the first cavity is achieved by dissolving the material.

8. The method of claim 3, wherein the first dissolvable material is one of: prolyvinyl alcohol (PVA), high impact polystyrene (HIPS), polylactic acid (PLA), acrylonitrile butadiene styrene (ABS), nylon, polycarbonate, glucose, glucose gelatin, polyethylene terephthalate (PET), polycarprolactone (PCL), low-density polyethylene (LDPE), high density polyethylene (HDPE), polymethylpentene (PMP), polypropylene (PP), polytetrafluoroethylene (PTFE), polyvinyl chloride (PVC), and mixtures thereof.

9. The method of claim 8, wherein dissolving the first dissolvable material comprises subjecting the first dissolvable material to a respective solvent.

10. The method of claim 9, wherein the solvent is one of: water, terpene, limonine, sodium hydroxide, acetone, acetic acid, dichloromethane, respective enzymes, acetaldehyde, acetic anhydride, acetone, hydrofluoric acid, trifluoroacetic acid, dilute acetic acid (50%), hydrochloric acid (37%), nitric acid, sulfuric acid, ethyl alcohol, isobutyl alcohol, methyl alcohol, n-butyl alcohol propyl alcohol, ammonium hydroxide, aniline, aqua regia, benzaldehyde, benzene, carbon tetrachloride, caustic soda (NaOH), chlorobenzene, chloroform, cyclohexane, esters, ether, diethyl ether, isopropyl ether, methyl ethyl, hexane, hydrazine, hydrogen peroxide, methylene chloride, petroleum ether, phenol, sodium hydroxide, tetrahydrofuran, toluene, trichloroethylene, trimethylpentane, xylene, and mixtures thereof.

11. The method of claim 1, wherein:
a second volume defines a body portion and a sprue portion that extends from the body portion to the external surface of the subassembly and thereby defines the first cavity; and
the introduction of the first additive material into the first cavity comprises introducing the additive material into the body portion through the sprue portion.

12. The method of claim 11, wherein:
the first volume and the second volume are defined such that when the first additive material is introduced into the second volume beyond a threshold extent, and the additive material achieves a solid state, the additive material provides sufficient structural support to maintain the spatial relationship between the first volume and the second volume when the first dissolvable material is dissolved.

13. The method of claim 12, wherein the first additive material is introduced into the second volume to the extent that the additive material conforms to the shape of at least a part of the sprue portion, and upon solidification, thereby provides sufficient structural support to maintain the spatial relationship between the first volume and the second volume when the first dissolvable material is dissolved.

14. The method of claim 11, wherein the subassembly comprises a volume that is defined by the presence of a material, where the material acts to support the subassembly when the first dissolvable material is dissolved and when the first additive material is introduced into the second volume.

15. The method of claim 14, further comprising removing the material that acts to support the subassembly when the first dissolvable material is dissolved and when the first additive material is introduced into the second volume.

16. The method of claim 15, wherein the removal of the material that acts to support the subassembly when the first dissolvable material is dissolved and when the first additive material is introduced into the second volume is achieved mechanically.

17. The method of claim 15, wherein the removal of the material that acts to support the subassembly when the first dissolvable material is dissolved and when the first additive material is introduced into the second volume is achieved by dissolving the material.

18. The method of claim 11, wherein the first dissolvable material is one of: prolyvinyl alcohol (PVA), high impact polystyrene (HIPS), polylactic acid (PLA), acrylonitrile butadiene styrene (ABS), nylon, polycarbonate, glucose, glucose gelatin, polyethylene terephthalate (PET), polycarprolactone (PCL), low-density polyethylene (LDPE), high density polyethylene (HDPE), polymethylpentene (PMP), polypropylene (PP), polytetrafluoroethylene (PTFE), polyvinyl chloride (PVC), and mixtures thereof.

19. The method of claim 18, wherein dissolving the first dissolvable material comprises subjecting the first dissolvable material to a respective solvent.

20. The method of claim 19, wherein the solvent is one of: water, terpene, limonine, sodium hydroxide, acetone, acetic acid, dichloromethane, respective enzymes, acetaldehyde, acetic anhydride, acetone, hydrofluoric acid, trifluoroacetic acid, dilute acetic acid (50%), hydrochloric acid (37%), nitric acid, sulfuric acid, ethyl alcohol, isobutyl alcohol, methyl alcohol, n-butyl alcohol propyl alcohol, ammonium hydroxide, aniline, aqua regia, benzaldehyde, benzene, carbon tetrachloride, caustic soda (NaOH), chlorobenzene, chloroform, cyclohexane, esters, ether, diethyl ether, isopropyl ether, methyl ethyl, hexane, hydrazine, hydrogen peroxide, methylene chloride, petroleum ether, phenol, sodium hydroxide, tetrahydrofuran, toluene, trichloroethylene, trimethylpentane, xylene, and mixtures thereof.

21. The method of claim 1, wherein the volume that defines a shape that is to exist in the object to be fabricated is occupied by solid material in the fabricated object.

\* \* \* \* \*